United States Patent [19]

Swift et al.

[11] Patent Number: 5,747,447
[45] Date of Patent: May 5, 1998

[54] STABLE POLYPEPTIDE COMPOSITION

[75] Inventors: Robert L. Swift; Charles P. Du Mee, both of Foster City; Anne Randolph, Burlingame, all of Calif.

[73] Assignee: COR Therapeutics, South San Francisco, Calif.

[21] Appl. No.: 462,661

[22] Filed: Jun. 5, 1995

Related U.S. Application Data

[63] Continuation of Ser. No. 55,636, Apr. 30, 1993, abandoned, which is a continuation-in-part of Ser. No. 876,625, Apr. 30, 1992, abandoned.

[51] Int. Cl.$^6$ .................. A61K 38/00; A61K 38/02; C07K 5/00; C07K 7/00
[52] U.S. Cl. .................. 514/9; 514/11; 514/2; 514/13; 514/14; 514/15
[58] Field of Search .................. 514/2, 9, 11, 13, 514/14, 15; 530/317, 325, 326, 324, 350; 930/260, 270

[56] References Cited

U.S. PATENT DOCUMENTS

| | | | |
|---|---|---|---|
| 4,361,510 | 11/1982 | Mitra | 260/112 |
| 4,470,968 | 9/1984 | Mitra et al. | 424/101 |
| 4,500,514 | 2/1985 | Nakanishi et al. | 424/94 |
| 5,099,003 | 3/1992 | Kotitschke et al. | 530/382 |
| 5,192,746 | 3/1993 | Lobl et al. | 514/11 |
| 5,384,309 | 1/1995 | Barker et al. | 514/11 |

FOREIGN PATENT DOCUMENTS

| | | |
|---|---|---|
| 0211592 | 2/1987 | European Pat. Off. . |
| 0286830 | 10/1988 | European Pat. Off. . |
| 0288891 | 11/1988 | European Pat. Off. . |
| 0311950 | 4/1989 | European Pat. Off. . |
| WO 83/04027 | 11/1983 | WIPO . |
| WO 90/15620 | 12/1990 | WIPO . |

OTHER PUBLICATIONS

Gomori, G., "Preparation of Buffers for Use in Enzyme Studies," *Methods in Enzymology*, Academic Press, NY (Colowick et al. eds.), pp. 138–146 (1955).

Green et al., "Protein Fractionation on the Basis of Solubility in Aqueous Solutions of salts and Organic Solvents," *Methods in Enzymology*, Academic Press, NY (Colowick et al. eds.), pp. 67–79 (1955).

Landaburu et al., "Pharmaceutical Preparation Containing Purified Fibronectin," CA 102:32301 (1984)—Abstract only.

Lehninger, A.L., *Biochemistry*, Worth Publishers, Inc., pt. 1, p. 162 (1975).

Manning et al. "Stability of Protein Pharmaceuticals," *Pharmaceutical Res.*, vol. 6, No. 11, pp. 903–918 (1989).

Nishimaki et al., "Stable Dried Preparations Containing Thrombin," *Pharmaceuticals*, vol. 113 (1990)—Abstract only.

Sugawara et al, "Pharmaceuticals Containing Stabilized Interleukin–1β," *Pharmaceuticals*, vol. 113 (1990)—Abstract only.

Yamada et al, "Stable Aqueous Carbacalcitonin Solutions Containing Gelatins for Treatment of Bone Disease," *Pharmaceuticals*, vol. 117 (1992)—Abstract only.

*Primary Examiner*—Avis M. Davenport
*Attorney, Agent, or Firm*—Cooley Godward LLP

[57] ABSTRACT

A (injectable biologically active) polypeptide is stabilized by dissolving said polypeptide forming a liquid solution in citrate buffer of about pH 5.0–5.5.

20 Claims, No Drawings

STABLE POLYPEPTIDE COMPOSITION

CROSS-REFERENCE TO RELATED APPLICATIONS

This application is a continuation of U.S. application Ser. No. 08/055,636, filed Apr. 30, 1993 now abandoned, which is a continuation-in-part of U.S. application Ser. No. 07/876,625, filed Apr. 30, 1992 now abandoned.

FIELD OF THE INVENTION

The present invention relates to stable polypeptide compositions and methods of preparing such stable compositions.

BACKGROUND OF THE INVENTION

Polypeptides possess chemical and physical properties that present special problems which can cause instability in storage and delivery, particularly of biologically active polypeptides. Usually polypeptides are lyophilized to form solid compositions. Often, additives are introduced into polypeptide formulations in an effort to increase stability. Such additives have included salts of ionic compounds, polyalcohols, but this is less effective at higher concentrations of such additive, and detergents, both nonionic and anionic, particularly for transdermal and intranasal administration. Many of the instability problems of protein pharmaceuticals are discussed in Manning et al., *Pharm. Res.* (1989) 6 (11): 903–918.

European patents 311,950, 286,830 and 288,891 and U.S. Pat. Nos. 4,361,510 and 4,470,968 describe separation processes that use of one or usually more than one of various additives such as 3-propiolactone; various Tris, hepes, glycine or citrate buffers, polyols or alkanols; salts, such as sodium chloride or sodium, potassium or lithium citrate, in preparing or purifying proteins but with a pH above at least 5.5 and preferably usually 6, if not 7–8. Usually the protein is removed from these additives and preferably lyophilized.

However, many polypeptides are useful as biologically active materials which are most useful when injected directly into an animal. This is the case for polypeptides useful as therapeutic agents for the treatment and prevention of platelet-associated ischemic disorders initiated by atherosclerosis and arteriosclerosis.

In treatment of some life-threatening results of these disorders it can be necessary to inject the patient with a drug concentrate as quickly as possible (bolus treatment) and/or followed by prolonged (infusion) treatment with a lower drug concentration. Accordingly, the drug, which may be a polypeptide, must be stored conveniently for immediate use by hospital personnel and paramedics. This means it must be storage-stable for long periods, even at room temperature, and already in an injectable liquid formulation, not a solid which must be dissolved.

Because the drug is injectable, it must be formulated as simply as possible to be as compatible as possible with the patient so as to not induce other traumas or interfere with other drugs being given to the patient. The ideal formulation would avoid other additives normally required for stabilization and be a ready-to-use liquid concentrate.

SUMMARY OF THE INVENTION

The present invention is directed to a method of stabilizing substantially pure polypeptide comprising forming a liquid solution consisting essentially of a substantially pure polypeptide in a citrate buffer, said solution having a pH of from about 5.0 to about 5.5, to stabilize said polypeptide. Preferably, the polypeptide is an injectable, biologically active polypeptide so that the stabilized composition can be used as a resulting therapeutically effective solution.

The invention also includes the resulting useful therapeutic compositions of an injectable biologically active, substantially pure polypeptide consisting essentially of a biologically effective amount of a substantially pure polypeptide in a liquid solution of a citrate buffer, said solution having a pH of from about 5.0 to about 5.5. Such compositions are capable of remaining very stable, for example, at about 4° C., for 7, 34 or 49 days prior to injection, are still stable at up to about 50° C. and have, greater stability at about 70° C. than compositions having a pH above 5.5. The compositions of the invention also remain stable (and injectable) at about −15° C. to about 30° C. for at least 90 days, preferably for at least 18 months and have improved stability at higher temperatures.

The resulting liquid composition can be aseptically introduced into sterile delivery vial, bag or bottle and sealed ready for injection on attachment of an injection device, such as a hypodermic needle or intravenous tube.

DETAILED DESCRIPTION OF THE INVENTION

The invention provides a method of stabilizing a substantially pure polypeptide in a liquid solution to be stable on storage at about −15° C. to about 30° C. for at least 90 days and, preferably, at least 18 months or to have improved stability at higher temperatures. The polypeptide is dissolved in the citrate buffer to form the solution.

By "substantially pure" is meant a polypeptide that has been purified to a pharmaceutically acceptable level of purity and preferably is essentially purified to homogenicity.

Polypeptides soluble in aqueous media are well known to those of skill in the art, including as described in U.S. Pat. No. 4,532,212 and includes derivatives such as enzymes and the like. Pharmaceutically useful polypeptides are well known to those of skill in the act as discussed in Manning, et al. *Pharmaceutical Research*, 6 (11): 903–918 (1989).

By "biologically active" is meant any polypeptide having an effect on a biological system. Such polypeptides include pharmaceutically active polypeptides, such as interferon, insecticidally active polypeptides, such as insecticidal *Bacillus thuringiensis* endotoxins, and the like. A wide variety of polypeptides are known in the art which have an effect on a biological system, in the case of pharmaceuticals the effect is therapeutic. In other cases the effect can be insecticidal, fungicidal or the like.

By "injectable" is meant that the polypeptide can be injected into a patient and a wide variety of such polypeptides are known to those of skill in the art.

By "biologically compatible citrate buffer" is meant a citrate buffer prepared from ingredients that do not themselves have an undesirable or adverse effect on a biological system. Such buffer components are well known to those of skill in the pharmaceutical art.

By "biological system" is meant a living entity including plants, animals or a living part thereof, such as an organ or cell. The preferred biological system is a mammalian system, especially a human system.

By "stability" or "improved stability" is meant herein that in the liquid solution of the invention, a high amount (e.g., by weight) of the substantially pure polypeptide remains substantially intact or more intact (that is physically and chemically stable and therefore biological activity when initially present is also stabilized) after a period of time under conditions of exposure to temperatures below 50° C., preferably below 30° C. and has improved stability even at about 70° C., and to light, oxygen and the storage container used for injectable biologically active substantially pure polypeptides. This stability can be evaluated by conventional assay methods applicable to purity, weight or size of polypeptides. These include not only visual evaluations, such as discoloration, transparency and precipitation, but can include assays normally applied to separate polypeptides from each other and from other materials, such as chromatography, e.g., reversed phase high performance liquid chromatography (HPLC), and ultraviolet (UV) analysis. Conventional biological assays can be used when the polypeptide is a biologically active one.

By "citrate buffer" is meant a conventional citrate solution to which large amounts of strong acid or base can be added with only very small resultant change in the hydrogen-ion concentration. The citrate buffer is prepared by methods known in the art by adding a pH-neutral strong electrolyte or a strong base to a citric acid solution. Suitable electrolytes include sodium chloride, sodium citrate, potassium nitrate, sodium hydrogen sulfate and the like. Suitable strong bases include sodium hydroxide, calcium hydroxide and the like, sodium hydroxide is preferred. Adjustment in ionic strength, pH concentration of polypeptide are made in the normal manner for making pH-adjusted isotonic solutions. Additions of ingredients to prepare the citrate buffer and compositions of the invention can be made in any order but preferably, the polypeptide is added to injectable grade water and then the buffer ingredients are added or especially when the polypeptide is added to a citric acid solution. In one embodiment, a solution of a concentration of about 200 mg of polypeptide per ml in 1.0M citric acid is formed, diluted to 85% of the final volume with water, the pH is adjusted to 5.0 to 5.5 using sodium hydroxide and then diluted to the final volume and concentration with water.

Additional ingredients which are conventionally employed in (pharmaceutical) preparations, such as glycine and other salts, can be present but are not essential ingredients in the compositions of the invention.

While a wide variety of biologically compatible buffers are known in the art, they are usually used with other additives at a pH above 5.5 and usually at a pH above 7, and even then lyophilized to a dry powder. However, it has now been found that citrate buffer solutions of a (biologically active) polypeptide having a pH of from about 5.0 to about 5.5 are unexpectedly very storage-stable over long periods of time without the addition of other ingredients or without other treatments such as lyophilization. In a preferred embodiment, the pH of the solution is from about 5.25.

The concentration of the substantially pure polypeptide in the citrate buffer is a stabilizing effective amount and can vary depending on a variety of factors including the specific polypeptide, pH and the specific buffer. The stabilizing effective amount of the citrate buffer and the concentration of polypeptide in a stabilized composition of the invention can readily be determined by those of skill in the protein formulation art. As a general matter, the concentration of the substantially pure polypeptide can be from about 0.01 to about 200 mg/ml and is usually about 0.01 to about 10 mg/ml. For injectable and/or biologically active polypeptides, the concentration in the composition can further be adjusted as can readily be determined by those of skill in the art to correspond to an effective dosage for the intended biological effect. For example, when the polypeptide is (SEQ ID NO:63) Mpr-L-homoarginine-Gly-Asp-Trp-Pro-Cys-NH$_2$•acetate or a cyclic form thereof, the concentration usually corresponds to a dosage of from about 0.5 to about 5 mg/ml, preferably from about 0.5 to about 2.0 mg/ml. A 0.5 mg/ml dosage form, which is a direct infusion pre-mix is a bolus followed by an infusion. The bolus is about 10 to about 500, preferably about 30–300 µg/Kg (about 1–40 mg, preferably from about 2–20 mg for a 70 Kg patient) and the infusion is 0.02–2 µg/Kg/min, but probably 0.5–1.0 µg/Kg/min (50–100 mg/day for a 70 Kg patient). Administration can be by injection from a bolus up to 7 days, preferably for about 12 hours to about 3 days depending on the indication.

Preferably the polypeptide is any biologically active, substantially pure polypeptide that can be injected into a patient for treatment can be stabilized by the method of the invention. The substantially pure polypeptides include linear and cyclic polypeptides of at least two amino acid residues and therefore includes simple linear dipeptides and large protein molecules. Preferably, the polypeptide is a synthetic or recombinant polypeptide.

In one preferred embodiment of the invention, the polypeptide contains up to 10 amino acid residues. An especially preferred polypeptide is (SEQ ID NO:63) Mpr-L-homoarginine-Gly-Asp-Trp-Pro-Cys-NH$_2$•acetate or a cyclic form thereof.

The substantially pure polypeptide can contain the usual polypeptide modifications such as disulfide bonds, ionic bonds, glycosylation and the like.

In one embodiment of the invention, the polypeptide has the formula

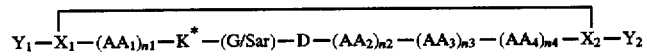

wherein K* has the formula

wherein (G/Sar) is G or Sar;

wherein each $R^1$ is independently H, alkyl(1–6 C), or at most one $R^1$ is $R^2$—C=NR$^3$, wherein $R^2$ is H, alkyl(1–6 C) or is a substituted or unsubstituted phenyl or benzyl residue, or is NR$^4_2$ in which each $R^4$ is independently H or alkyl(1–6 C), and $R^3$ is H, alkyl(1–6 C), phenyl or benzyl, or $R^2$—C=NR$^3$ is a radical selected from the group consisting of

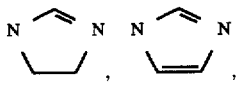

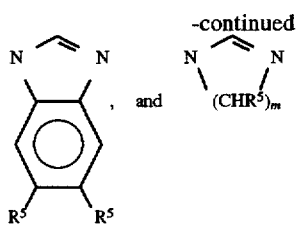

where m is an integer of 2–3, and each $R^5$ is independently H or alkyl(1–6 C);

and wherein one or two ($CH_2$) may be replaced by O or S provided said O or S is not adjacent to another heteroatom;

$AA_1$ is a small, neutral (polar or nonpolar) amino acid and N1 is an integer of 0–3;

$AA_2$ is a neutral, nonpolar large (aromatic or nonaromatic) or a polar aromatic amino acid and n2 is an integer of 0–3;

$AA_3$ is a proline residue or a modified proline residue and n3 is an integer of 0–1;

$AA_4$ is a neutral, small amino acid or the N-alkylated form thereof and n4 is an integer of 0–3;

each of $X_1$ and $X_2$ is independently a residue capable of forming a bond between $X_1$ and $X_2$ to obtain a cyclic compound as shown; and each of $Y_1$ and $Y_2$ is independently a noninterfering substituent or may be absent;

wherein one or more peptide linkages may optionally be replaced by a linkage selected from the group consisting of —$CH_2NH$—, —$CH_2S$—, —$CH_2CH_2$—, —CH=CH—(cis and trans), —$COCH_2$—, —CH(OH)$CH_2$— and —$CH_2SO$—.

Suitable peptides of the invention include those wherein $Y_1$, is H, acyl, or a peptide residue or derivatized form thereof or is absent and $Y_2$ is OH, $NH_2$ or a peptide residue or derivatized form thereof or is absent, $Y_2$ is $NH_2$—A—$NH_2$ or is absent, $X_1$ and $X_2$ are selected from the group consisting of cysteine (C), mercaptopropionyl (Mpr) and penicillamine (Pen), $AA_1$ is G and $n_1$ is 0 or 1, $AA_2$ is selected from the group consisting of W, F, L, Y, and V and K* is K, Har, acetimidyl-Lys or phenylimidyl-Lys. In one embodiment, the polypeptides have the above formula with the proviso that if n3 is 0; either:

1) the sum of n2 and n4 must be at least 2; or
2) K* must be other than Har or K; or
3) at least one of $X_1$ and $X_2$ must be other than cys (C), penicillamine (Pen), or 2-amino-3,3-cyclopentanemethylene-3-mercaptopropionic acid (APmp); or
4) $Y_1$ or $Y_2$ must comprise at least one amino acid residue; or
5) one or more linkages is replaced by said alternate linkage.

Examples of suitable peptides include (SEQ ID NO:1)
Mpr-K-G-D-W(Formyl)-P-C-$NH_2$
(SEQ ID NO:2)
Mvl-K-G-D-W-P-C-$NH_2$
(SEQ ID NO:3)
Mpr-K-G-D-W-P-Pen-$NH_2$
(SEQ ID NO:4)

Mpr(Acetimidyl-Lys)-G-D-W-P-C-$NH_2$
(SEQ ID NO:5)
Mpr(Acetimidyl-Lys)-G-D-W-P-Pen-$NH_2$
(SEQ ID NO:6)
Mpr(Phenylimidyl-Lys)-G-D-W-P-C-$NH_2$
(SEQ ID NO:7)
Mpr(Phenylimidyl-Lys)-G-D-W-P-Pen-$NH_2$
(SEQ ID NO:8)
Mpr-Ala-(Har)-G-D-W-P-C-$NH_2$
(SEQ ID NO:9)
Mpr-L-homoarginine-Gly-Asp-Trp-Pro-Cys-$NH_2$
(SEQ ID NO:10)
Mpr-K-G-D-W-P-C-$NH_2$ or cyclic forms thereof.

Such peptides are described in copending U.S. application Ser. No. 07/483,229, filed Feb. 20, 1990 and PCT/US90/03417 published as WO90/15620, each incorporated herein by reference and described in further detail in the following 35 pages and examples 4–14.

"Alkyl" is conventionally defined as a straight or branched chain or cyclic hydrocarbyl residue of the indicated number of carbon atoms such as methyl, ethyl, isopropyl, N-hexyl, 2-methylbutyl, cyclohexyl and the like.

The benzyl and phenyl residues represented by $R^2$ may be unsubstituted, or may be substituted by noninterfering substituents. Preferred substitution patterns are those wherein only one substituent is bound to the aromatic nucleus, preferably in the 4-position. Preferred substituents are electron donating substituents such as alkyl (1–6 C), especially ethyl or methyl, or phenyl.

Preferred embodiments of K* include the residues of lysine, homoarginine, formylhomoarginine, ornithine, acetimidyl lysine, $N^GN^G$ ethylene-homoarginine, and phenylimidyl lysine. The phenylimidyl lysyl residue, for example, has the formula:

As the essential feature of the preferential inhibition of binding appears to reside in the substitution of K* for R of (SEQ ID NO:11) RGDX, one class of peptides or peptide of the formula

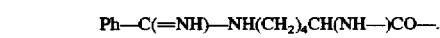

As the essential feature of the preferential inhibition of binding appears to reside in the substitution of K* for R of (SEQ ID NO:11) RGDX, one class of peptides or peptide-related compounds for use in the compositions of the invention comprises naturally occurring platelet aggregation inhibitors (PAI) which ordinarily contain RGDX in the binding sequence whereby these forms are modified by substituting K* for R in this sequence. Included are the native peptides having this substitution, as well as their fragments of sufficient length to be effective in selectively inhibiting the binding of adhesive proteins to GP IIb-IIIa and fragments or full-length peptides which have irrelevant substitutions in positions of the peptide which do not destroy this activity. For the most part, the fragments will contain residues corresponding to the length of a peptide chain of at least 7 amino acids if the conformation is controlled by, for example, cyclization, and are of greater length if there is no such conformational control. In general, aside from the K*GDX required sequence, there may be 1–10, preferably 14, and preferably 1–3 amino acid substitutions in the non-K*GDX portion of the peptides.

Additionally, the G of (SEQ ID NO:11) RGDX or (SEQ ID NO:12) K*GDX can be replaced by a sarcosine residue.

In addition, one or more of the peptide bonds can be optionally replaced by substitute linkages such as those obtained by reduction or elimination. Thus, one or more of the —CONH— peptide linkages can be replaced with other types of linkages such as —CH$_2$NH—, —CH$_2$S—, CH$_2$CH$_2$—, CH=CH— (cis and trans), —COCH$_2$—, —CH(OH)CH$_2$ and —CH$_2$SO—, by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F. in "Chemistry and Biochemistry of Amino Acids, Peptides and Proteins." B. Weinstein, eds., Marcel Dekker, New York, p. 267 (1983) (general review); Morley, J. S., Trends Pharm Sci (1980) pp. 463–468 (general review); Hudson, D. et al. Int J Pept Prot Res (1979) 14:177–185 (—CH$_2$NH—, CH$_2$CH$_2$—); Spatola, A. F. et al., Life Sci (1986) 38:1243–1249 (—CH$_2$—S); Hann, M. M. J Chem Soc Perkin Trans I (1982) 307–314 (—CH—CH—, cis and trans); Almquist, R. G., et al., J Med Chem (1980) 23: 1392–1398 (—COCH$_2$); Jennings-White, C. et al. Tetrahedron Lett (1982) 23:2533 (—COCH$_2$—); Szelke, M., et al., European Appln. EP 45665 (1982) CA: 97:39405 (1982) (—CH(OH)CH$_2$—); Holladay, M. W. et al. Tetrahedron Lett (1983) 24:4401–4404 (—C(OH)CH$_2$—); and Hruby, V. J. Life Sci (1982) 31:189–199 (—CH$_2$—S—). Particularly preferred is —CH$_2$NH—.

Examples of fragments and/or modified forms of the naturally-occurring snake venom PAI include [E$^{28}$, L$^{41}$, C$^{64}$]barbourin(28–73) of the sequence Still an additional group of examples includes that wherein the glycyl residue of RGD or K*GD can be replaced by a sarcosyl residue with retention of activity. Thus, the active PAIs which are isolated and/or modified in other ways as described above may further be modified by this substitution.

While fragments and/or modified PAIs from snake venom can be included among the Fg/vWF/GP IIb-IIa binding-specific compounds by replacing RGD by K*GD, in additional embodiments specifically active peptides are based on compatible extensions of the K*GD sequence per se.

Y$_1$ and Y$_2$ can be peptide extensions of 0–25 amino acid residues and can be in derivatized form. The Y$_1$ N-terminal extensions can, for example, be acetylated or otherwise acylated; the Y$_2$ C-terminal extension can be amidated with NH$_2$ or with a primary or secondary amine of the formula R-NH$_2$ or R$_2$NH wherein each R is independently a lower alkyl of 1–4 C, such as methyl, n-butyl, or t-butyl. Y$_1$ can also be (H) or acyl (1–4 C); Y$_2$ can be (OH), NH$_2$ or an amine as above. Where the compound of formula (1) is a simply cyclic peptide, Y$_1$ and Y$_2$ are absent.

X$_1$ and X$_2$ are typically amino acid residues capable of cyclization such as, for example and most preferably, cysteine residues capable of forming a disulfide ring. However, other residues capable of forming disulfide or other linkages can also be used—for example, the Pen (penicillamine) residue described by Pierschbacher et al. (supra) or the Mpr (mercapto propionyl) or Mvl (mercaptovaleryl) residue. Other types of covalent linkages for cyclization envisioned include peptide linkages, as for example, an amide formed

```
1                                              46
ECADGLCCDQCRFLKKGTVCRVAKGDWNDDTCTGQSCDCPRNGLYG    (SEQ ID NO: 13)
28                                             73
``` and [K$^{29}$]eristicophin(4–51) of the sequence

```
4                                               51
EEPCATGPCCRRCKFKRAGKVCRVAKGDWNNDYCTGKSCDCPRNPWNG   (SEQ ID NO: 14).
4                                               51
```

In this notation, the size of the fragment is noted in parentheses after the name by the numbers of the amino acids which are included in the fragment, and the bracketed prefix letters and numbers indicate amino acid substitutions at the numbered positions in the native full-length peptide. Thus, for the barbourin fragment above, the length of the fragment spans residues 28–73 inclusive of the native sequence and the amino acids originally in positions 28, 41 and 64 of the numbered native sequence have been replaced by Glu (E), Leu (L), and Cys (C), respectively.

As additional examples, the arginine of the RGD sequence appearing in trigramin, elegantin, albolabrin, crotatroxin, flavoviridin, echistatin, bitistatin, viridin, molossin, lutosin, basilicin, applagin, halysin, horridin, tergeminin, lachesisn, cotiarin, cereberin, jararacin, kistrin, eristicophin, bitan-a, and ruberin/oreganin can be replaced by a K* residue to provide specifically active PAIs with a preferential affinity for GP IIb-IIIa. In addition, shortened forms of these peptides, containing at least 20, preferably at least 30, and more preferably at least 40, amino acids, can be prepared from the native peptide or in this modified form. In addition, or in the alternative, 1–10, preferably 1–4, amino acids irrelevant to the RGD/K*GD sequence can be substituted or modified, preferably with conservative amino acid substitutions. By conservative amino acid substitutions is meant, for example, substitution of an acidic amino acid residue for an acidic amino acid residue, neutral for neutral, basic for basic, etc., as is further described hereinbelow.

between the side-chain amino group of a lysyl residue with a side-chain carboxyl group of a glutamyl residue and ester linkages, such can be formed between a side-chain alcohol of a threonine residue with a side-chain carboxyl of an aspartyl residue. Any compatible residue capable of forming peptide bonds with the remainder of the chain (or modified peptide bonds as described above) and capable of covalent bond formation to effect cyclization can be used. This includes, for example, simply cyclic peptides, wherein a peptide bond is directly formed between the NH$^2$ at the N-terminus and the COOH at the C-terminus.

As described above, one or more of the indicated peptide bonds may be replaced by a substitute linkage such as —CH$_2$NH—, —CH$_2$S—, CH$_2$CH$_2$—, —CH=CH—(cis and trans), —COCH$_2$—, —CH(OH)CH$_2$— and —CH$_2$SO—.

In the designation of the amino acid residues AA$_1$–AA$_4$ above, description has been made on the basis of a classification method, wherein amino acid residues can be generally subclassified into four major subclasses. This classification is also shown diagrammatically hereinbelow.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or nonpolar is arbitrary, and, therefore, amino acids specifically contemplated have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows (see also the diagram below).

Acidic: Aspartic acid and Glutamic acid;

Basic/noncyclic: Arginine, Lysine;

Basic/cyclic: Histidine;

Neutral/polar/small: Glycine, Serine and Cysteine;

Neutral/polar/large/nonaromatic: Threonine, Asparagine, Glutamine;

Neutral/polar/large/aromatic: Tyrosine;

Neutral/nonpolar/small: Alanine;

Neutral/nonpolar/large/nonaromatic: Valine, Isoleucine, Leucine, Methionine;

Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this defined group, but is classified separately. AA$_3$ is designated a proline residue or a "modified proline residue." Proline, as is understood, is a five-membered nitrogen heterocycle with a carboxyl group in the 2-position. Modified proline residues are all nitrogen five or six-membered heterocycles with carboxyl groups in the position alpha to the nitrogen; additional heterocyclic atoms may also be included in the ring. Thus, modified proline residues include residues of pipecolic acid (2-carboxypiperidine, abbreviated Pip) and thiazolidine (Thz). Thus, proline or modified proline residues are of the formula

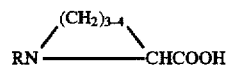

wherein one or two of the methylene groups may be replaced by NR, S, or O and where any ring nitrogen can optionally be substituted with R as a noninterfering substituent such as alkyl (1–6 C).

Certain commonly encountered amino acids, which are not encoded by the genetic code, include, for example, beta-alanine (beta-ala), or other omega-amino acids, such as 3-amino propionic, 4-amino butyric and so forth, alpha-aminoisobutyric acid (Aib), sarcosine (Sar), ornithine (Orn), citrulline (Cit), homoarginine (Har), t-butylalanine (t-BuA), t-butylglycine (t-BuG), N-methylisoleucine (N-MeIle), phenylglycine (Phg), and cyclohexylanine (Cha), norleucine (Nle), cysteic acid (Cya); pipecolic acid (Pip), thiazolidine (Thz), 2-naphthyl alanine (2-Nal) and methionine sulfoxide (MSO). These also fall conveniently into particular categories.

Based on the above definition,

Sar and beta-ala are neutral/nonpolar/small;

t-Bua, t-BuG, N-MeIle, Nle and Cha are neutral/nonpolar/large/nonaromatic;

Cya is acidic;

Cit, Acetyl Lys, and MSO are neutral/polar/large/nonaromatic;

2-Nal and Phg are neutral/nonpolar/large/aromatic; and

Pip an Thz are modified proline residues.

The foregoing may be shown diagrammatically as follows:

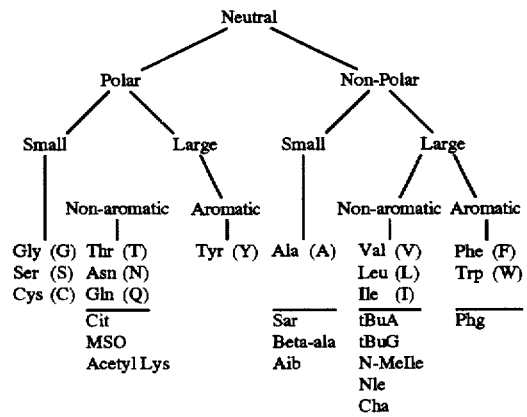

The various omega-amino acids are classified according to size as neutral/nonpolar/small (beta-ala, i.e., 3-aminopropionic, 4-aminobutyric) or large (all others).

Other amino acid substitutions for those encoded in the gene can also be included in peptide compounds within the scope of the invention and can be classified within this general scheme.

In the formulas representing selected specific embodiments of the present invention, the amino-and carboxyl-terminal groups, although often not specifically shown, will be understood to be in the form they would assume at physiological pH values, unless otherwise specified. Thus, the N-terminal $H^+_2$ and C-terminal-$O^-$ at physiological pH are understood to be present thought not necessarily specified and shown, either in specific examples or in generic formulas. Of course, the basic and acid addition salts including those which are formed at nonphysiological pH values are also included. Unless otherwise noted, the residues are in the L-form; in generic formulas, the specified residues can be either L- or D-. Generally, the polypeptides of the invention have 0, 1, or 2 D-residues included, preferably 0 or 1, most preferably 0. In the polypeptides shown, each encoded residue where appropriate is represented by a single letter designation, corresponding to the trivial name of the amino acid, in accordance with the following conventional list:

| Amino Acid | One-Letter Symbol |
| --- | --- |
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |
| Pyroglutamic acid | Z |

The amino acids not encoded genetically are abbreviated as indicated above.

In the specific peptides shown in the present application, the L-form of any amino acid residue having an optical isomer is intended unless otherwise expressly indicated by a dagger superscript (†). While the residues of the peptides are normally in the natural L optical isomer form, one or two, preferably one, amino acid may be replaced with the optical isomer D form.

Free functional groups, including those at the carboxy- or amino-terminus, can also be modified by amidation, acylation or other substitution, which can, for example, change the solubility of the compounds without affecting their activity.

In forming amidated peptides of the present invention, the analog compounds can be synthesized directly, for example using BOC-AA$_X$-pMBHA-Resin or Boc-AA$_X$-BHA-Resin, wherein AA$_X$ is the selected carboxy-terminal amino acid of the desired peptide as described in further detail below. Alternatively, the peptides can be chemically or enzymatically amidated subsequent to peptide synthesis using means well known to the art, or prepared by standard solution-phase peptide synthesis protocols.

Certain embodiments of the de novo peptides of the invention are preferred. In the K$^+$(G/Sar)D sequence, G/Sar is preferably G. AA1 and AA$_4$ are preferably Gly, Ala or Ser; n1 is preferably 0–2, n4 is preferably 1–2. Preferred for AA$_2$ are neutral/nonpolar/aromatic amino acids, especially tryptophan and phenylalanine, particularly tryptophan. n$_2$ is preferably 1. X$_1$ and X$_2$ are preferably Cys, Mpr, or Pen (penicillamine) residues. Y$_1$ is preferably H, acetyl,or Gly; Y$_2$ is preferably —NH$_2$ or —A—NH$_2$. Also preferred generally are C-terminal amidated forms of Y$_2$.

Thus, preferred embodiments of the PAI analogs include peptides of the following formulas. Although all of these are capable of provision in cyclic form through formation of disulfide linkages, these linkages are not specifically shown; other cyclic forms are noted by "cyclo."

|   | Preferred Peptides |   |
| --- | --- | --- |
| (SEQ ID NO:15) | PAI 1: | E-C-A-D-G-L-C-C-D-Q-C-R-F-L-K-K-G-T-V-C-R-V-A-K-G-D-W-N-D-D-T-C-T-G-Q-S-C-D-C-P-R-N-G-L-Y-G |
| (SEQ ID NO:16) | PAI 2: | E-E-P-C-A-T-G-P-C-C-R-R-C-K-F-K-R-A-G-K-V-C-R-V-A-K-G-D-W-N-N-D-Y-C-G-K-S-C-D-C-P-R-N-P-W-N-G |
| (SEQ ID NO:17) | PAI 3: | G-C-G-K-G-D-W-P-C-A-NH$_2$ |
| (SEQ ID NO:18) | PAI 4: | G-C-K-G-D-W-P-C-A-NH$_2$ |
| (SEQ ID NO:19) | PAI 5: | C-G-K-G-D-W-P-C-NH$_2$ |
| (SEQ ID NO:20) | PAI 7: | C-K-G-D-W-C-A-NH$_2$ |
| (SEQ ID NO:21) | PAI 9: | Mpr-K-G-D-Pen-NH$_2$ |
| (SEQ ID NO:22) | PAI 10: | C-K-G-D-W-P-C-NH$_2$ |
| (SEQ ID NO:23) | PAI 12: | C-K-G-D-Y-P-C-NH$_2$ |
| (SEQ ID NO:24) | PAI 13: | C-K-G-D-F-P-C-NH$_2$ |
| (SEQ ID NO:25) | PAI 14: | C-K-G-D-L-P-C-NH$_2$ |
| (SEQ ID NO:26) | PAI 15: | C-K-G-D-V-P-C-NH$_2$ |
| (SEQ ID NO:27) | PAI 16: | C-K-G-D-Y(OMe)-P-C-NH$_2$ |
| (SEQ ID NO:28) | PAI 17: | C-K-G-D-(2-Nal)-P-C-NH$_2$ |
| (SEQ ID NO:29) | PAI 18: | C-K-G-D-(Cha)-P-C-NH$_2$ |
| (SEQ ID NO:30) | PAI 19: | Mpr-K-G-D-W-P-C-NH$_2$ |
| (SEQ ID NO:31) | PAI 20: | Mpr-K-G-D-Y-P-C-NH$_2$ |
| (SEQ ID NO:32) | PAI 21: | Mpr-K-G-D-F-P-C-NH$_2$ |
| (SEQ ID NO:33) | PAI 22: | Mpr-K-G-D-L-P-C-NH$_2$ |
| (SEQ ID NO:34) | PAI 23: | Mpr-K-G-D-V-P-C-NH$_2$ |
| (SEQ ID NO:35) | PAI 24: | Mpr-K-G-D-Y(OMe)-P-C-NH$_2$ |
| (SEQ ID NO:36) | PAI 25: | Mpr-K-G-D-(2-Nal)-P-C-NH$_2$ |
| (SEQ ID NO:37) | PAI 26: | Mpr-K-G-D-(Cha)-P-C-NH$_2$ |
| (SEQ ID NO:38) | PAI 27: | cyclo(G-K-G-D-W-P) |
| (SEQ ID NO:39) | PAI 28: | cyclo(A-K-G-D-W-P) |
| (SEQ ID NO:40) | PAI 29: | cyclo(D-Ala-K-G-D-W-P) |
| (SEQ ID NO:41) | PAI 30: | cyclo(F-K-G-D-W-P) |
| (SEQ ID NO:42) | PAI 31: | cyclo(beta-Ala-K-G-D-W-P) |
| (SEQ ID NO:43) | PAI 32: | cyclo(gamma-Abu-K-G-D-W-P) |
| (SEQ ID NO:44) | PAI 33: | cyclo(R-K-G-D-W-P) |
| (SEQ ID NO:45) | PAI 34: | C-K-G-D-W-G-C-NH$_2$ |
| (SEQ ID NO:46) | PAI 37: | C-K-A-D-W-P-C-NH$_2$ |
| (SEQ ID NO:47) | PAI 39: | C-K-G-D-W-(Sar)-C-NH$_2$ |
| (SEQ ID NO:48) | PAI 41: | C-K-G-D-I-P-C-NH$_2$ |
| (SEQ ID NO 49) | PAI 42: | C-K-G-D-(4-Cl-Phe)-P-NH$_2$ |
| (SEQ ID NO 50) | PAI 43 | C-K-(Sar)-D-W-P-C-NH$_2$ |
| (SEQ ID NO:51) | PAI 44: | C-K-G-D-(4-NO$_2$-Phe)-P-C-NH$_2$ |
| (SEQ ID NO:52) | PAI 47: | Acetyl-C-K-G-D-W-P-C-NH$_2$ |
| (SEQ ID NO:53) | PAI 48: | Mpr-K-G-D-W(Formyl)-P-C-NH$_2$ |
| (SEQ ID NO:54) | PAI 49: | Mvl-K-G-D-W-P-C-NH$_2$ |
| (SEQ ID NO:55) | PAI 51: | Mpr-K-G-D-W-P-Pen-NH$_2$ |
| (SEQ ID NO:56) | PAI 52: | Mpr-K-G-D-W-P-Pen†-NH$_2$ |
| (SEQ ID NO:57) | PAI 54: | Mpr-K-G-D -W-P-Pen-NH$_2$ |
| (SEQ ID NO:58) | PAI 55: | Mpr-K-G-D-W-(Thz)-C-NH$_2$ |
| (SEQ ID NO:59) | PAI 56: | Mpr-K-G-D-H(2,4-DNP)-P-C-NH$_2$ |
| (SEQ ID NO:60) | PAI 57: | Mpr-K-G-D-(2-Nal)-P-Pen-NH$_2$ |
| (SEQ ID NO:61) | PAI 58: | Mvl-K-G-D-W-P-Pen-NH$_2$ |
| (SEQ ID NO:62) | PAI 59: | Mpr-K-G-D-W-(Pip)-Pen-NH$_2$ |
| (SEQ ID NO:63) | PAI 60: | Mpr-(Har)-G-D-W-P-C-NH$_2$ |
| (SEQ ID NO:64) | PAI 61: | Mpr-K-G-D-W-P-C†-NH$_2$ |
| (SEQ ID NO:65) | PAI 62: | Mpr-K†-G-D-W-P-Pen-NH$_2$ |
| (SEQ ID NO:66) | PAI 63: | Mpr-(Har)-G-D-W-P-Pen-NH$_2$ |
| (SEQ ID NO:67) | PAI 64: | Mpr-(Acetimidyl-Lys)-G-D-W-P-C-NH$_2$ |
| (SEQ ID NO:68) | PAI 65: | Mpr-(Acetimidyl-Lys)-G-D-W-P-Pen-NH$_2$ |
| (SEQ ID NO:69) | PAI 66: | Mpr-(N$^G$,N$^{G'}$-ethylene-Har)-G-D-W-P-C-NH$_2$ |
| (SEQ ID NO:70) | PAI 67: | Mpr-(N$^G$,N$^{G'}$-ethylene-Har)-G-D-W-P-Pen-NH$_2$ |
| (SEQ ID NO:71) | PAI 68: | Mpr-Har-Sar-D-W-P-C-NH$_2$ |
| (SEQ ID NO:72) | PAI 69: | Mpr-(Acetimidyl-Lys)-G-D-W-P-Pen-NH$_2$ |
| (SEQ ID NO:73) | PAI 70: | Mpr-(Phenylimidyl-Lys)-G-D-W-P-C-NH$_2$ |

-continued

Preferred Peptides

| | | |
|---|---|---|
| (SEQ ID NO:74) | PAI 71: | Mpr-Har-Sar-D-W-P-Pen-NH$_2$ |
| (SEQ ID NO:75) | PAI 72: | Mpr-(Phenylimidyl-Lys)-G-D-W-P-Pen-NH$_2$ |
| (SEQ ID NO:76) | PAI 73 | Mpr-Har-G-D-W-(3,4-dehydro-Pro)-C-NH$_2$ |
| (SEQ ID NO:77) | PAI 74 | Mpr-Har-G-D-Pen-NH$_2$ |
| (SEQ ID NO:78) | PAI 75 | Mpr-(Phenylimidyl-Lys)-G-D-Pen-NH$_2$ |
| (SEQ ID NO:79) | PAI 80 | Mpr-P-Har-G-D-W-P-C-NH$_2$ |
| (SEQ ID NO:80) | PAI 81 | Mpr-G-Har-G-D-W-P-C-NH$_2$ |
| (SEQ ID NO:81) | PAI 82 | Mpr-A-Har-G-D-W-P-C-NH$_2$ |
| (SEQ ID NO:82) | PAI 83 | Mpr-Aib-Har-G-D-W-P-C-NH$_2$ |
| (SEQ ID NO:83) | PAI 84 | Mpr-(N-Me-Arg)-Har-G-D-W-P-C-NH$_2$ |
| (SEQ ID NO:84) | PAI 85 | Mpr-(N-Me-Ser)-Har-G-D-W-P-C-NH$_2$ |
| (SEQ ID NO:85) | PAI 86 | Mpr-A†-Har-G-D-W-P-C-NH$_2$ |
| (SEQ ID NO:86) | PAI 87 | Mpr-(β-Ala)-Har-G-D-W-P-C-NH$_2$ |
| (SEQ ID NO:87) | PAI 88 | Mpr-(N-Me-Leu)-Har-G-D-W-P-C-NH$_2$ |
| (SEQ ID NO:88) | PAI 89 | Mpr-(N-Me-Ala)-Har-G-D-W-P-C-NH$_2$ |
| (SEQ ID NO:89) | PAI 90 | Mpr-Sar-Har-G-D-W-P-C-NH$_2$ |
| (SEQ ID NO:90) | PAI 91 | Mpr-V-Har-G-D-W-P-C-NH$_2$ |
| (SEQ ID NO:91) | PAI 92 | Mpr-S-Har-G-D-W-P-C-NH$_2$ |
| (SEQ ID NO:92) | PAI 93 | Mpr-Har-G-D-W-P-A-C-NH$_2$ |
| (SEQ ID NO:93) | PAI 94 | Mpr-Har-G-D-W-P-(N-Me-Ala)-C-NH$_2$ |
| (SEQ ID NO:94) | PAI 95 | Mpr-Har-G-D-W-P-G-C-NH$_2$ |
| (SEQ ID NO:95) | PAI 96 | Mpr-Har-G-D-W-P-A-†-C-NH$_2$ |
| (SEQ ID NO:96) | PAI 97 | Mpr-Har-G-D-W-P-C-NH$_2$ |
| (SEQ ID NO:97) | PAI 98 | Mpr-Har-G-D-W-P-(Sar)-C-NH$_2$ |
| (SEQ ID NO:98) | PAI 99 | Mpr-Har-G-D-W-P-(Aib)-NH$_2$ |
| (SEQ ID NO:99) | PAI 100 | Mpr-A-(Har)-G-D-W-P-Pen-NH$_2$ |
| (SEQ ID NO:100) | PAI 101 | Mpr-A-K-G-D-W-P-Pen-NH$_2$ |
| (SEQ ID NO:101) | PAI 102 | Mpr-D-(Har)-G-D-W-P-Pen-NH$_2$ |
| (SEQ ID NO:17) | PAI 3: | G-C-G-K-G-D-W-P-C-A-NH$_2$ |
| (SEQ ID NO:18) | PAI 4: | G-C-K-G-D-W-P-C-A-NH$_2$ |
| (SEQ ID NO:19) | PAI 5: | C-G-K-G-D-W-P-C-NH$_2$ |
| (SEQ ID NO:21) | PAI 9: | Mpr-K-G-D-Pen-NH$_2$ |
| (SEQ ID NO:22) | PAI 10: | C-K-G-D-W-P-C-NH$_2$ |
| (SEW ID NO:23) | PAI 12: | C-K-G-D-Y-P-C-NH$_2$ |
| (SEQ ID NO:24) | PAI 13: | C-K-G-D-F-P-C-NH$_2$ |
| (SEQ ID NO:30) | PAI 19: | Mpr-K-G-D-W-P-C-NH$_2$ |
| (SEQ ID NO:36) | PAI 25: | Mpr-K-G-D-(2-Nal)-P-C-NH$_2$ |
| (SEQ ID NO:45) | PAI 34: | C-K-G-D-W-G-C-NH$_2$ |
| (SEQ ID NO:47) | PAI 39: | C-K-G-D-W-(Sar)-C-NH$_2$ |
| (SEQ ID NO:49) | PAI 42: | C-K-G-D-(4-Cl-Phe)-P-NH$_2$ |
| (SEQ ID NO:50) | PAI 43: | C-K-(Sar)-D-W-P-C-NH$_2$ |
| (SEQ ID NO:51) | PAI 44: | C-K-G-D-(4-NO$_2$-Phe)-P-C-NH$_2$ |
| (SEQ ID NO:52) | PAI 47: | Acetyl-C-K-G-D-W-P-C-NH$_2$ |
| (SEQ ID NO:53) | PAI 48: | Mpr-K-G-D-W(Formyl)-P-C-NH$_2$ |
| (SEQ ID NO:54) | PAI 49: | Mvl-K-G-D-W-P-C-NH$_2$ |
| (SEQ ID NO:55) | PAI 51: | Mpr-K-G-D-W-P-Pen-NH$_2$ |
| (SEQ ID NO:56) | PAI 52: | Mpr-K-G-D-W-P-(D-Pen)-NH$_2$ |
| (SEQ ID NO:58) | PAI 55: | Mpr-K-G-D-W-(Thz)-C-NH$_2$ |
| (SEQ ID NO:59) | PAI 56: | Mpr-K-G-D-H(2,4-DNP)-P-C-NH$_2$ |
| (SEQ ID NO:60) | PAI 57: | Mpr-K-G-D-(2-Nal)-P-Pen-NH$_2$ |
| (SEQ ID NO:61) | PAI 58: | Mvl-K-G-D-W-P-Pen-NH$_2$ |
| (SEQ ID NO:62) | PAI 59: | Mpr-K-G-D-W-(Pip)-Pen-NH$_2$ |
| (SEQ ID NO:63) | PAI 60: | Mpr-(Har)-G-D-W-P-C-NH$_2$ |
| (SEQ ID NO:64) | PAI 61: | Mpr-K-G-D-W-P-C†-NH$_2$ |
| (SEQ ID NO:65) | PAI 62: | Mpr-K†-G-D-W-P-Pen-NH$_2$ |
| (SEQ ID NO:66) | PAI 63: | Mpr-(Har)-G-D-W-P-Pen-NH$_2$ |
| (SEQ ID NO:67) | PAI 64: | Mpr-(Acetimidyl-Lys)-G-D-W-P-C-NH$_2$ |
| (SEQ ID NO:68) | PAI 65: | Mpr-(Acetimidyl-Lys)-G-D-W-P-Pen-NH$_2$ |
| (SEQ ID NO:69) | PAI 66: | Mpr (N$^G$,N$^{G'}$-ethylene-Har)-G-D-W-P-C-NH$_2$ |
| (SEQ ID NO:70) | PAI 67: | Mpr (N$^G$,N$^{G'}$-ethylene-Har)-G-D-W-P-Pen-NH$_2$ |
| (SEQ ID NO:71) | PAI 68: | Mpr-Har-Sar-D-W-P-C-NH$_2$ |
| (SEQ ID NO:72) | PAI 69: | Mpr-(Acetimidyl-Lys)-G-D-W-P-Pen-NH$_2$ |
| (SEQ ID NO:73) | PAI 70: | Mpr-(Phenylimidyl-Lys)-G-D-W-P-C-NH$_2$ |
| (SEQ ID NO:74) | PAI 71: | Mpr-Har-Sar-D-W-P-Pen-NH$_2$ |
| (SEQ ID NO:75) | PAI 72: | Mpr-(Phenylimidyl-Lys)-G-D-W-P-Pen-NH$_2$ |
| (SEQ ID NO:76) | PAI 73: | Mpr-Har-G-D-W-(3, 4-dehydro-Pro)-C-NH$_2$ |

Chemical Synthesis of the Invention Peptides

Polypeptides within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups such as fluorenylmethyloxycarbonyl (Fmoc), are suitable. For example, Boc-Gly-OH, Boc-Ala,OH, Boc-His (Tos) —OH, (i.e., selected carboxy-terminal amino acids) can be esterified to chloromethylated polystyrene resin supports, p-methyl benzhydrylamine (pMBHA) or PAM resins. The polystyrene resin support is preferably a copolymer of styrene with about 0.5 to 2% divinyl benzene as a crosslinking agent which causes the polysterene polymer to be completely insoluble in certain organic solvents. See Stewart, et al., *Solid-Phase Peptide Synthesis* (1969) W. H. Freeman Co., San Francisco and Merrifield *J Am Chem Soc* (1963) 85:2149–2154. These and other methods of peptide synthesis are also exemplified by U.S. Pat. Nos. 3,862,925, 3,842,067, 3,972,859, and 4,105,602.

The synthesis can use manual synthesis techniques or automatically employ, for example, an Applied BioSystems 430A or 431A Peptide Synthesizer (Foster City, Calif.) following the instructions provided in the instruction manual supplied by the manufacturer. Cleavage of the peptides from the resin can be performed using the "low-high" HF deprotection protocols as described in Lu, G.-S., et al., *Int J Peptide & Protein Res* (1987) 29:545–557. Refolding of analogs of the snake venom PAIs can be performed using the procedure outlined in Garsky, V., et al., *Proc natl Acad Sci USA* (1989) 86:4022–4026 which describes the solid-phase synthesis of echistatin.

The cyclic peptides of this invention which do not have disulfide bonds can be conveniently prepared by a combination of solid phase synthesis and formation of the cyclic ring structure in solution using the general methods as outlined in U.S. Pat. No. 4,612,366 to Nutt. Thus, linear peptides prepared on standard Merrifield resin can be cleaved from the resin with hydrazine, followed by cyclization of the corresponding azide to form the cyclic peptides.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

Recombinant Production

Alternatively, selected polypeptides of the present invention can be produced by expression of recombinant DNA constructs prepared in accordance with well-known methods. Such production can be desirable to provide large quantities or alternative embodiments of such compounds. Since the peptide sequences are relatively short, recombinant production is facilitated; however, production by recombinant means is particularly preferred over standard solid phase peptide synthesis for peptides of at least 8 amino acid residues.

The DNA encoding the sequenced polypeptide, such as a PAI, is preferably prepared using commercially available nucleic acid synthesis methods. Methods to construct expression systems for production of PAI in recombinant hosts are also generally known in the art.

Expression can be effected in either procaryotic or eucaryotic hosts. Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, a workhorse vector for *E. coli* is pBR322 and its derivatives. Commonly used procaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived $P_L$ promoter and N-gene ribosome binding site. However, any available promoter system compatible with procaryotes can be used.

Expression systems useful in eucaryotic hosts comprise promoters derived from appropriate eucaryotic genes. A class of promoters useful in yeast, for example, includes promoters for synthesis of glycolytic enzymes, e.g., those for 3-phosphoglycerate kinase. Other yeast promoters include those from the enolase gene or the Leu2 gene obtained from YEp13.

Suitable mammalian promoters include the early and late promoters from SV40 or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter, for example, is appropriate.

The expression systems are constructed using well-known restriction and ligation techniques and transformed into appropriate hosts.

Transformation is done using standard techniques appropriate to such cells. The cells containing the expression systems are cultured under conditions appropriate for production of the polypeptide, e.g., PAI and the polypeptide, e.g., PAI, is then recovered and purified.

Antibodies

The availability of the purified polypeptide, e.g., PAI, of the invention also permits the production of antibodies specifically immunoreactive with these forms of the active peptide.

For example, the compositions containing purified PAI isolated from snake venom or otherwise synthesized can be used to stimulate the production of antibodies which immunoreact with the PAI peptide. Standard immunization protocols involving administering PAI to various vertebrates, such as rabbits, rats, mice, sheep, and chickens result in antisera which are immunoreactive with the purified peptide. Polypeptide, e.g., PAI, may be advantageously conjugated to a suitable antigenically neutral carrier, such as an appropriate serum albumin or keyhole limpet hemocyanin, in order to enhance immunogenicity. In addition, the free peptide can be injected with methylated BSA as an alternative to conjugation. Furthermore, the antibody-secreting cells of the immunized mammal can be immortalized to generate monoclonal antibody panels which can then be screened for reactivity with the polypeptide, such as PAI.

The resulting polyclonal or monoclonal antibody preparations are useful in assays for levels of the corresponding polypeptide, e.g., PAI, in biological samples using standard immunoassay procedures.

Active PAI Assay

The identification of snake venom starting material which contains active PAI, and which PAI has known specificity, is made possible by the PAI assay. The PAI assay rests on the observation that compounds which block the binding of fibrinogen to the GP IIb–IIIa complex in vitro also are capable of inhibiting thrombin or ADP-induced aggregation of human platelets and the formation of platelet-thrombi in vivo. This observation provides the basis for obtaining potent PAIs by evaluating the ability of test materials to disrupt fibrinogen-GP IIb-IIIa interactions.

In the assay, GP IIb-IIIa, prepared in purified form, for example as described by Fitzgerald, L. A., et al., *Anal Biochem* (1985) 151:169–177, incorporated herein by reference, is coated onto a solid support such as beads, test tubes, or microtiter plates. The coated support is then contacted with fibrinogen and with the test material and incubated for a sufficient time to permit maximal binding of fibrinogen to the immobilized GP IIb-IIIa. Fibrinogen is typically provided at a concentration of about 5–50 nM and the test material can, if desired, be added at a series of dilutions. Typical incubations are 2–4 hr at 35° C., the time and temperature being interdependent.

After incubation, the solution containing the fibrinogen and test material is removed and the level of binding of fibrinogen measured by quantitating bound fibrinogen to GP IIb-IIIa. Any suitable means of detection can be used, but it is convenient to employ labeled fibrinogen, for example using radioactive, fluorescent or biotinylated labels. Such methods are well known and need not be elaborated here.

Assessment of the results is aided by employing a control sample, usually identical to the test sample except that the test substance is absent. In this case, percent inhibition may be calculated using the basis, so that $$\% \text{ inhibition} = \frac{\text{control} - \text{test}}{\text{control}} \times 100.$$

Other measures of inhibition effectiveness, such as $IC_{50}$, can also be used.

The PAI assay systems further include characterization of the PAI specificity by binding inhibition assays identical to that above but substituting other adhesive proteins for Fg and other receptors for GP IIb-IIIa. In particular, inhibition of the binding of vitronectin to the vitronectin receptor; fibronectin to the fibronectin receptor; fibronectin to GP IIb-IIIa and fibrinogen and/or vWF to GP IIb-IIIa can be assessed. The adhesive protein and receptors for these assays are available in the art.

Other Assays

In addition to the above plate assays, other assays for platelet aggregation inhibition activity and related activities are also available, as set forth above. In summary, a list of commonly employed assays is as follows:

1. The plate assays utilizing specific receptors described in the previous paragraphs;
2. Standard assays directly applied to platelet aggregation, such as those described by Gann, Z.-R., et al., *J Biol Chem* (1988) 263:19827–19832; Huang, T. F., et al., *J Biol Chem* (1987) 262:16157–16163; *Biochemistry* (1989) 28:661–666, cited above and incorporated herein by reference;
3. An in vivo thrombosis model in dogs as described by Folts, J. D., et al., *Circulation* (1976) 54:365; and
4. Effect on cell adhesion using S35 methionine-labeled cells as described hereinbelow in Example 10.

Administration and Utility of PAIs

The PAIs of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation on vessel walls.

The PAIs can be used for prevention or abortion of arterial thrombus formation, in unstable angina and arterial emboli or thrombosis, as well as treatment or preventions of myocardial infarction (MI) and mural thrombus formation post MI. For brain-related disorders, treatment or prevention of transient ischemic attack and treatment of thrombotic stroke or stroke-in-evolution are included.

The PAIs can also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention can be used in numerous nontherapeutic applications where inhibiting platelet aggregation is desired. For example, improved platelet and whole blood storage can be obtained by adding sufficient quantities of the peptides, the amount of which will vary depending upon the length of proposed storage time, the conditions of storage, the ultimate use of the stored material, etc.

The PAI dosage can range broadly depending upon the desired affects and the therapeutic setting. Typically, dosages can be a 0.5 mg/ml dosage form, which is a direct infusion pre-mix is a bolus followed by an infusion. The bolus is about 10 to about 500, preferably about 30–300 μg/Kg (about 1–40 mg, preferably from about 2–20 mg for a 70 Kg patient) and the infusion is 0.02–2 μg/Kg/min, but probably 0.5–1.0 μg/Kg/min (50–100 mg/day for a 70 Kg patient). Administration is preferably parenteral, such as intravenous on a daily basis for up to a week or as much as one or two months or more, all of which will vary with the peptide's size. If the peptides are sufficiently small (e.g., less than about 8–10 amino acid residues) other routes of administration can be utilized, such as intranasally, sublingually, or the like.

Injectables can be prepared in conventional forms, either as liquid solutions or suspensions, solid forms suitable for solution or suspension in liquid prior to injection, or as emulsions.

The invention also includes novel therapeutic compositions consisting essentially of an injectable biologically active substantially pure polypeptide as a liquid solution in a citrate buffer, said solution having a pH of from about 5.0 to about 5.5. The compositions are capable of remaining very stable at about 4° C., are still stable even at about 50° C. and have improved stability at about 70° C. for 7, 34 or 49 days prior to injection as compared to compositions having a pH greater than about 5.5. The compositions of the invention also remain stable and injectable at about −15° C. to about 30° C. for at least 18 months.

The therapeutic compositions contain any injectable biologically active substantially pure polypeptide as discussed above. Preferably the substantially pure polypeptide is biologically active for inhibiting thrombus formation, preventing platelet loss during extracorporeal circulation of blood or for treating a patient suspected of having a platelet-associated ischemic syndrome. In one preferred embodiment, the polypeptide is a cyclic polypeptide containing up to 10 amino acid residues, and preferably at least one disulfide bond, such as (SEQ ID NO:53) Mpr-K-G-D-W(Formyl)-P-C-NH$_2$, (SEQ ID NO:54) Mvl-K-G-D-W-P-C-NH$_2$, (SEQ ID NO:55) Mpr-K-G-D-W-P-Pen-NH$_2$ (SEQ ID NO:63) Mpr-(Har)-G-D-W-P-C-NH$_2$, (SEQ ID NO:66) Mpr-(Har)-G-D-W-P-Pen-NH$_2$ (SEQ ID NO:67) Mpr (Acetimidyl-Lys)-G-D-W-P-C-NH$_2$, (SEQ ID NO:68) Mpr (Acetimidyl-Lys)-G-D-W-P-Pen-NH$_2$, (SEQ ID NO:73) Mpr(Phenylimidyl-Lys)-G-D-W-P-C-NH$_2$, (SEQ ID NO:75) Mpr(Phenylimidyl-Lys)-G-D-W-P-Pen-NH$_2$, ( SEQ ID NO:81) Mpr-Ala-(Har)-G-D-W-P-C-NH$_2$, (SEQ ID NO:63) Mpr-L-homoarginine-Gly-Asp-Trp-Pro-Cys-NH$_2$, (SEQ ID NO:30) Mpr-K-G-D-W-P-C-NH$_2$, or cyclic forms thereof. Preferably, the polypeptide is (SEQ ID NO:63) Mpr-L-homoarginine-Gly-Asp-Trp-Pro-Cys-NH$_2$·acetate or a cyclic form thereof.

In another aspect, the invention includes novel PAI in isolated form which is identified in, and can be isolated form, active snake venom according to the methods of the invention. In particular, the invention relates to PAI, in isolated form, which can be isolated from *Echis colorata, Eristicophis macmahonii; A. hypnale, A. acutus, A. piscivorous leucostoma, A. piscivorous conanti; Bothrops asper; Bothrops cotiara, B. jararaca, B. iararacussu, B. lansbergi, B. medusa, B. nasuta, B. neuwiedi, B. pradoi, B. schlegli; Crotalus atrox, C. basilicus, C. cerastes cerastes, C. durissus durissus, C. durissus totonatacus, C. horridus horridus, C. molossus mollossus, C. ruber ruber, C. viridis cereberus, Crotalus v. helleri, Crotalus v. lutosus, Crotalus v. oreganus, Crotalus v. viridis; Lachesis mutas; Sistrurus catenatus tergeminus,* and *Sistrurus milarus barbouri.*

Preferred are PAIs in isolated form prepared from, or having the amino acid sequences of, those obtained from *Eristicophis macmahonii* (eristicophin); *Bothrops cotiara* (cotiarin); *B. jararacussu; Crotalus atrox* (crotatoxin); *C. basilicus* (basilicin); *C. cerastes cerastes* (cerastin); *C. durissus totonatacus* (durissin); *C. durissus durissus* (durissin); *C. h. horridus* (horridin); *Crotalus m. mollossus* (molossin); *C. ruber ruber* (ruberin); *Crotalus viridis lutosus* (lutosin); *C. v. viridis* (viridin); *Crotalus v. oreganus* (oreganin); *Crotalus v. helleri; Lachesis mutas* (lachesin); *Sistrurus catenatus tergeminus* (tergeminin); and *S. milarus barbouri* (barbourin).

Especially preferred are eristocophin, cotiarin, crotatroxin, cerastin, durissin, horridin, ruberin, lachesin, basilicin, lutosin, molossin, oreganin, viridin, tergeminin and barbourin.

The invention also includes peptides of the amino acid sequences as described above which are truncated and/or modified forms of the naturally occurring peptides and/or have one or more peptide linkages replaced by alternate linkages such as —CH$_2$NH— or —CH$_2$CH$_2$—.

In another aspect, the invention relates to PAI in isolated form which can be prepared from active snake venom identified by the method of the invention, and shown to specifically inhibit the binding fibrinogen (Fg) and/or von Willebrand Factor (vWF) to GP IIb-IIIa, and their truncated and/or modified forms.

In still another aspect, the invention relates to PAI of snake venom in isolated form wherein the sequence responsible for binding to the adhesive protein receptor includes the sequence KGD.

In another aspect, the invention is directed to a group of peptides or peptide-related compounds in general which are platelet aggregation inhibitors that are capable of inhibiting binding of Fg or vWF to GP IIb-IIIa at a substantially higher potency than that at which they inhibit binding of vitronectin to vitronectin receptor or fibronectin to fibronectin receptor. These peptides are characterized by having the binding sequence (SEQ ID NO:12) K*GDX in place of the (SEQ ID NO:11) RGDX binding sequence which is found in other PAI proteins. K* is a substituted or unsubstituted lysyl-derived residue of the formula R$^1_2$N(CH$_2$)$_4$CH(NH)CO— wherein each R$^1$ is independently H or a substituent which is sufficiently electron donating so as to not destroy the basicity of the adjacent nitrogen, and wherein one or two of the methylene residues may optionally be substituted by O or S, as described below. The barbourin PAI isolated from *S. milarus barbouri* is one illustration of this series of peptides. However, shorter forms of this peptide can also be used, as well as analogous sequences which also contain 1-10 amino acid residue modifications elsewhere in the peptide chain, and/or replacement of peptide linkages with alternate linkages. Other illustrative embodiments include isolated PAI peptides having a negative (SEQ ID NO:11) RGDX sequence wherein this is replaced by (SEQ ID NO:12) K*GDX. As in the case of barbourin, these isolated PAI may be otherwise in native form, or may be truncated and/or may contain 1-10 amino acid residue substitutions or deletions, and/or may have non-peptide linkages substituted for peptide linkages.

Another group of compounds which falls within the scope of the invention is that wherein the foregoing compounds are as described, except that the glycyl residue in the RGD or K*GD sequence is replaced by a sarcosyl residue. This class of compounds retains the potency and specificity of the related RGD or K*GD-containing peptides.

The platelet aggregation inhibitors (PAI) of the invention include low molecular weight peptides which can be prepared in isolated form, as described below, from snake venom which has been identified as "active," i.e., has been found to contain PAI using the method of the invention, which is described hereinbelow.

The invention method permits ready identification and characterization of the presence of an effective PAI in snake venom which selectively inhibits binding to GP IIb-IIIa as opposed to other integrins as, for example, the vitronectin receptor and the fibronectin receptor. Upon such identification, and, optionally and optimally, characterization, the PAI can be isolated and purified using a variety of standard techniques illustrated herein and disclosed in the art. For example, a combination of separation based on molecular weight (typically recovery of substances of <10 kd), ion exchange chromatography, and reverse phase HPLC can be used. Other techniques can also be employed, but a workable procedure applicable to PAI from any active snake venom is as follows:

About 10–1000 mg venom is dissolved in dilute acetic acid and applied to a sizing column, such as Sephadex G-50, and eluted in the same solvent. Fractions are assayed for activity using the Fg/GP IIb-IIIa binding assay of the invention, a standard platelet aggregation assay (PAA) or any similar assay relying on the adhesive protein binding activity of GP IIb-IIIa. Alternatively, the <10 kd fraction of the fraction of the venom can be recovered using ultrafiltration and similarly assayed.

The low MW fraction isolated by either procedure is then loaded onto a preparative C-18 HPLC column, such as a C-18 Delta Pak reverse phase HPLC column, available from Waters, preequilibratd in 0.1% trifluoroacetic acid (TFA)/ 8% acetonitrile. The adsorbed PAI is then eluted using a gradient of 8%-60% acetonitrile in 0.1% TFA. The slope of the gradient and flow rate are optimized using routine procedures. Active fractions are determined by PAA or by the disclosed receptor binding method. The active fractions are then pooled, concentrated, and tested for homogeneity using analytical HPLC or SDS-PAGE. Further reverse-phase HPLC gradient purification is applied until the recovered PAI is homogenous.

It is understood that the isolated PAI of determined sequence can, when synthesized in vitro, be modified by sequence alterations which do not destroy activity. In general, these modified forms will differ from the native forms by 1-10, preferably 1-4, amino acid substitutions or will be truncated forms. In addition, one or more peptide linkages may be replaced by alternate linkages as described herein. A particularly preferred substitution is replacement of RGD by K*GD to confer GP IIb-IIIa specificity as described herein.

The PAI of *Sistrurus m. barbouri* has been purified to homogeneity and sequenced, and termed "barbourin". Unlike the adhesive proteins for GP IIb-IIIa so far identified and the peptides from snake venoms that block GP IIb-IIIa function, barbourin does not contain the standard Arg-Gly-Asp sequence of the adhesive proteins known in the art. The apparent binding sequence in barbourin is (SEQ ID NO:102) Lys-Gly-Asp-(Trp). The presence of the KGD sequence in the apparent binding region of this peptide is especially surprising in view of the observation that replacement of Lys for Arg in small synthetic peptides based on the (SEQ ID NO:103) RDGX sequence greatly decreases the ability of these peptides to bind to integrin receptors (Pierschbacher et al., *Proc Natl Acad Sci* (USA)(1984) 81:5985–5988; Williams et al., *Thromb Res* (1987) 46:457–471); Huang et al., *J. Biol Chem* (1987) 262:16157–16163. It is thought that this substitution may in part be responsible for the specificity of the barbourin peptide to inhibit Fg and vWF binding to GP IIb-IIIa, versus, for example, inhibition of vitronectin binding to the vitronectin receptor.

EXAMPLES

The invention is illustrated by the following examples which should not be regarded as limiting the invention in any way.

Example 1

Preparation of Stabilized Composition

Citrate buffer solution is prepared by mixing citric acid in a volumetric flask to give a final citrate concentration of 25 mM with Nanopure water and adding NaOH to adjust the pH.

To the above citrate buffer solution was added 200 ng of greater than 95% pure cyclic form of Mpr-L-homoarginine-Gly-Asp-Trp-Pro-Cys-NH$_2$·acetate polypeptide (I) to give a solution concentration of 2 mg/ml when adjusted to the desired pH.

Stability Determination

One ml aliquots of the above solution of polypeptide in citrate buffer were sealed in borosilicate glass ampules under sterile conditions and stored at a constant temperature. Test sample ampules from each pH and temperature condition 4° C., 50° C. and 70° C. were removed periodically, visually assessed and then analyzed separately by HPLC using a mobile phase comprising acetonitrile (MeCN) and 0.1% trifluoroacetic (TFA) in water. This stability was evaluated by conventional assay methods applicable to purity, weight or size of polypeptides. These included not only visual evaluations, such as discoloration, transparency and precipitation, and included assays normally applied to separate polypeptides from each other and from other materials by reversed phase high performance liquid chromatography (HPLC).

Results of these experiments are set forth in Table 1 in which the stability is expressed in terms of the percentage of main peak of original polypeptide found in the sample analyzed by HPLC. The composition was also found to be normal on visual evaluation.

TABLE 1

Peptide Stability in Citrate Buffer Composition

| | 4° C. | | | 50° C. | | | 70° C. | | |
|---|---|---|---|---|---|---|---|---|---|
| Time (min) | pH = 5.0 | 5.5 | 6.0 | pH = 5.0 | 5.5 | 6.0 | pH = 5.0 | 5.5. | 6.0 |
| 21.0 | 100 | 100 | 100 | 99 | 100 | 98 | 99 | 96 | 94 |
| 45.5 | 100 | 99 | 98 | 97 | 95 | 94 | 91 | 88 | 83 |
| 167.5 | 100 | 99 | 98 | 98 | 99 | 97 | 80 | 80 | 68 |
| 503.5 | 98 | 99 | 96 | 94 | 92 | 89 | 47 | 51 | 33 |
| 837.5 | 100 | 101 | 100 | 95 | 94 | 88 | 29 | 36 | 20 |
| 1173.5 | 100 | 101 | 100 | 92 | 92 | 83 | 17 | 22 | 13 |

Results of these experiments demonstrate that liquid solutions of I in citrate buffer having a pH of 5.00 and 5.50 were unexpectedly very stable at about 4° C., still stable at up to about 50° C. and much more stable at 70° C. in comparison to citrate buffer solutions at pH 6.0.

Example 2

Preparation of Stabilized Compositions

A solution was formed in water of a peptide of the invention (greater than 95% pure cyclic form of (SEQ ID NO:63) Mpr-L-homoarginine-Gly-Asp-Trp-Pro-Cys-NH$_2$·acetate polypeptide (I). To this solution was added about 1.6 mg/ml of citric acid monohydrate followed by about 5.1 mg/ml of sodium citrate dihydrate to give a final citrate solution concentration of 25 nM in water for injection and a final polypeptide concentration of about 2 mg/ml.

Stability Determination 20 ml aliquots of the above solution were placed into Type I glass vials and sealed with rubber stoppers and aluminum closures under sterile conditions and stored at a constant temperature. Test sample vials from each temperature condition, −15° C., 5° C., 30° C. and 45° C. were removed periodically and individually assessed and analyzed for stability by HPLC and visual evaluation as described in Example 1. Results of these experiments are set forth in Table 2 below.

TABLE 2

Peptide Stability in 5.5 pH Citrate Buffer Composition

| Time (days) | 5° C. | −15° C.* | 30° C.* | 45° C.* |
|---|---|---|---|---|
| 0 | 98.8 | — | — | — |
| 45 | — | 98.9 | 97.4 | 96.1 |
| 76 | 98.6 | — | — | — |
| 95 | — | 99.0 | 96.4 | 94.1 |
| 126 | 98.5 | — | — | — |
| 191 | — | 99.1 | 95.8 | 92.4 |
| 222 | 98.5 | — | — | — |
| 270 | — | 98.7 | 95.1 | 89.8 |
| 301 | 98.2 | — | — | — |
| 368 | — | 98.6 | 94.5 | 86.5 |
| 399 | 98.2 | — | — | — |
| 541 | — | 98.9 | 93.6 | 76.1 |
| 572 | 98.2 | — | — | — |

*After one month at 5° C., these samples were placed at the assigned temperature.

Results of these experiments demonstrated that liquid solutions of the polypeptide of the invention in citrate buffer having a pH of 5.25 were very stable from about −15° C. to about 30° C. The composition was also found to be normal by visual evaluation.

Example 3

Stability Determination

Following procedures similar to those described in Examples 1 and 2 above, (SEQ ID NO:81) Mpr-Ala-(Har)-G-D-W-P-C-NH$_2$ was dissolved in 25 mM citrate buffer at pH 5.25 at a concentration of about 1 mg/mL and stored in test sample vials at 5° C., 30° C. and 45° C. for up to 90 days. Test sample vials from each temperature condition were removed periodically and analyzed for stability by HPLC and visual inspection as described in Example 1. Results of these experiments are set forth in Table 3 below.

TABLE 3

| Time (Days) | 5° C. | 30° C. | 45° C. |
|---|---|---|---|
| 0 | 99.6 | — | — |
| 29 | 98.1 | 97.3 | 95.4 |
| 60 | 98.3 | 97.3 | 92.6 |
| 90 | 97.3 | 96.5 | 90.6 |

Results of these experiments demonstrated that liquid solutions of the polypeptide of the invention having a pH of 5.25 were very stable from about 5° C. to about 45° C. The composition was also found to be normal on visual evaluation.

Example 4

Preparation of Analog #1[E$^{28}$L$^{41}$C$^{64}$]barbourin (28–73):
(SEQ ID NO:15) E-C-A-D-G-L-C-C-D-O-C-R-F-L-K-K-G-T-V-C-R-V-A-K-G-D-W-N-D-D-T-C-T-G-O-S-C-D-C-P-R-N-G-L-Y-G One-half mmol of PAM-Gly resin (0.6 meq/g, Applied Biosystems, Foster City, Calif.) was subjected to Procedure A with the required amino acids (introduced in order). The Boc-protected amino acids had the following side-chain protection: Arg(Tos), Asp(OcHex), Cys(4-MeBzl), Glu (OcHex), Lys(Cl-Z), Thr(OBzl), Trp(CHO), and Tyr(Br-Z). Following assembly of the completed protected peptide-resin chain, the amino terminal Boc- group was removed with TFA and the resin dried as its TFA-salt form. The resin (1.3 g) was subjected to "low-high" HF deprotection protocols followed by removal of HF "in vacuo." The dried peptide-resin mixture was transferred to a fretted funnel (coarse) with ethyl ether and was washed several times with alternate washes of ether and chloroform to remove most of the organic protecting groups and scavengers used in the deprotection.

The Peptide mixture was transferred to 2 L of 0.4% acetic acid and the pH adjusted to 7.99 with concentrated NH$_4$OH.

The resin was filtered from this solution and the solution allowed to sit at 4° C. without stirring for 20 hr. This was followed by warming the solution to room temperature and storing for 3 days again without stirring. Precipitated material was removed by filtration and the supernatant pH adjusted to 3.0 with acetic acid and lyophilized.

The crude material was dissolved in 8.0 ml of 0.5M acetic acid and loaded onto a Sephadex G-50 fine column (2.5×100 cm) equilibrated with 0.5M acetic acid. The column was run at 20 ml/hr and fractions (4 ml) were collected into polypropylene tubes. Aliquots of fractions were dried, resuspended in water and tested for platelet aggregation inhibitory activity as previously described. Active fractions (71–90) were pooled and lyophilized.

Dried material (66 mg) was redissolved in 2.0 ml of 0.1M acetic acid and loaded onto the Waters Preparative C-18 column equilibrated with 8% acetonitrile containing 0.1% TFA. A gradient running from 8% acetonitrile to 20% in 10 minutes followed by a slow gradient to 30% acetonitrile in 40 min was performed. The column was eluted at 18 ml/min and fractions (12 sec) were collected into polypropylene tubes. Fractions were concentrated on a Speed-Vac concentrator to 1.0 ml volume and 10 ul aliquots were tested in the platelet aggregation assay.

Active fractions (29–32) were individually lyophilized and analyzed on the analytical C-18 HPLC column with an 8–30% acetonitrile gradient. Fractions 29 and 30 were pooled and loaded onto the analytical column in 1.0 ml of 0.5% TFA. The major peak was collected manually and lyophilized to yield 1.6 mg of pure peptide.

Amino acid analysis of this material confirmed the identity of the peptide. Assay of this material for its ability to inhibit the binding of fibrinogen to GP IIb-IIIa and vitronectin demonstrated that the high affinity of this analog for GP IIb-IIIa and the relative lack of affinity for VnR at concentrations up to 1 uM.

Example 5
Preparation of Analog #2,[$K^{29}$]eristicophin (4–51):

(SEQ ID NO:16) E-E-P-C-A-T-G-P-C-C-R-R-C-K-F-K-R-A-G-K-V-C-R-V-A-K-G-D-W-N-N-D-Y-C-T-G-K-S-C-D-C-P-R-N-P-W-N-G

One-half mmol of PAM-Gly resin (0.6 meq/g, Applied Biosystems, Foster City, Calif.) was subjected to Procedure A with the required amino acids (introduced in order). The Boc-protected amino acids had the following side-chain protection: Arg(Tos), Asp(OcHex), Cys(4-MeBzl), Glu(OcHex), Lys(Cl-Z), Ser(OBzl), Thr(OBzl), Trp(CHO), and Tyr(Br-Z). Cleavage, refolding and purification of this peptide was identical to the previous example. Receptor binding data for this analog are shown in FIGS. 26 and 28 in WO 90/15620.

Example 6
Preparation of Analog #3:

(SEQ ID NO:17) G-C-G-K-G-D-W-P-C-A-NH$_2$

One-half mmol of PMBHA resin (0.72 meq/g, Applied Biosystems, Foster City, Calif.) was subjected to Procedure A with the required amino acids (introduced in order). The Boc-protected amino acids had the following side-chain protection: Asp(O-cHex), Cys(4-Mebzl), and Lys(Cl-z). Following completion of the assembly of the protected peptide-resin, the amino terminal Boc group was removed with TFA and the resin dried as its TFA-salt form. The resin (1.54 g) was treated with anhydrous hydrogen fluoride (HF) containing 10% anisole, 2% ethyl methyl sulfide for 30 min at −10° C., and an additional 30 min at 0° C. The HF was removed in vacuo and the peptide/resin mixture was suspended in diethyl ether followed by alternately washing with chloroform and ether 3x. After a final ether wash, the peptide was extracted from the resin with 2.0M acetic acid, diluted with distilled water and lyophilized.

The crude peptide (370 mg) was dissolved in deoxygenated 10 mM NH$_4$OAc, pH 8, to 0.5 mg/ml and allowed to oxidize by dropwise addition of a slight excess of 0.01M potassium ferricyanide (K$_3$Fe(CN)$_6$) solution, stirred an additional 20 min, and adjusted to pH 5 with acetic acid. The peptide solution was treated with DOWEX AG3×4 anion-exchange resin for 15 min with stirring and the resin filtered, diluted with H$_2$O and lyophilized to yield the crude cyclized peptide. The crude cyclized peptide (392 mg) was purified by desalting on Sephadex G-25F using 0.5M acetic acid as eluent, followed by ion-exchange chromatography on CM-Sepharose (Pharmacia) using an elution gradient generated by addition of 100 mM NH$_4$OAc to a solution of 10 mM NH$_4$OAc, pH 4.5. Fractions which had a minimum purity of 90% by HPLC analysis were pooled and lyophilized from H$_2$O several times to yield 175 mg. Final purification consisted of preparative HPLC purification on a Water C-18 reverse-phase column with an acetonitrile/water/TFA gradient to yield purified peptide. Receptor binding data for this analog are shown in FIGS. 26, 29 and 30 in WO 90/15620.

Example 7

Preparation of Additional Analogs

The following analogs were synthesized; in most cases in a manner similar to that set forth in Example 6. However, analog 60, shown below, was prepared in solution via guanidation of the side chain of the lysine residue of analog #19 using eh procedure of Majusz, S., et al., *FEBS Letts* (1980) 110:85–87.

One mg of analog #19 was reacted with 1 mg of 1-amidino-3, 5-dimethylpyrazole nitrate (Aldrich) in 1 ml of absolute ethanol in the presence of diisopropylethylamine (DIEA) at room temperature for 4 days. The product analog 60 was purified from excess reagent and starting materials by reversed-phase HPLC on a C-18 column using a gradient of acetonitrile in 0.1% trifluoroacetic acid. Nine hundred ug of this material was isolated in purified form.

| | | |
|---|---|---|
| (SEQ ID NO:18): | #4: | G-C-K-G-D-W-P-C-A-NH$_2$ |
| (SEQ ID NO:19) | #5: | C-G-K-G-D-W-P-C-NH$_2$ |
| (SEQ ID NO:110) | #6: | G-C-G-K-G-D-W-C-A-NH$_2$ |
| (SEQ ID NO:20) | #7: | G-C-K-G-D-W-C-A-NH$_2$ |
| (SEQ ID NO:111) | #8: | Acetyl-C-K-G-D-C-NH$_2$ |
| (SEQ ID NO:21) | #9: | Mpr-K-G-D-Pen-NH$_2$ |
| (SEQ ID NO:22) | #10: | C-K-G-D-W-P-C-NH$_2$ |
| (SEQ ID NO:112) | #11: | Acetyl-C-R-G-D-Pen-NH$_2$ |
| (SEQ ID NO:23) | #12: | C-K-G-D-Y-P-C-NH$_2$ |
| (SEQ ID NO:24) | #13: | C-K-G-D-F-P-C-NH$_2$ |
| (SEQ ID NO:30) | #19: | Mpr-K-G-D-W-P-C-NH$_2$ |
| (SEQ ID NO:45) | #34: | C-K-G-D-W-G-C-NH$_2$ |
| (SEQ ID NO:113) | #35: | C-K-G-E-W-P-C-NH$_2$ |
| (SEQ ID NO:114) | #36: | C-Orn-G-D-W-P-C-NH$_2$ |
| (SEQ ID NO:46) | #37: | C-K-A-D-W-P-C-NH$_2$ |
| (SEQ ID NO:115) | #38: | C-K-A†-D-W-P-C-NH$_2$ |
| (SEQ ID NO:47) | #39: | C-K-G-D-W-(Sar)-C-NH$_2$ |
| (SEQ ID NO:116) | #40: | C-K(Formyl)-G-D-W-P-C-NH$_2$ |
| (SEQ ID NO:48) | #41: | C-K-G-D-I-P-C-NH$_2$ |
| (SEQ ID NO:49) | #42: | C-K-G-D-(4-Cl-Phe)-P-NH$_2$ |

-continued

| | | |
|---|---|---|
| (SEQ ID NO:50) | #43: | C-K-(Sar)-D-W-P-C-NH$_2$ |
| (SEQ ID NO:51) | #44: | C-K-G-D-(4-NO$_2$-Phe)-P-C-NH$_2$ |
| (SEQ ID NO:117) | #45: | C-K-G-D-(NMePhe)-P-C-NH$_2$ |
| (SEQ ID NO:118) | #46: | C-H-G-D-W-P-C-NH$_2$ |
| (SEQ ID NO:52) | #47: | Acetyl-C-K-G-D-W-P-C-NH$_2$ |
| (SEQ ID NO:53) | #48: | Mpr-K-G-D-W(Formyl)-P-C-NH$_2$ |
| (SEQ ID NO:54) | #49: | Mvl-K-G-D-W-P-C-NH$_2$ |
| (SEQ ID NO:119) | #50: | Mpr-K-G-D-W†-P-Pen-NH$_2$ |
| (SEQ ID NO:55) | #51: | Mpr-K-G-D-W-P-Pen-NH$_2$ |
| (SEQ ID NO:56) | #52: | Mpr-K-G-D-W-P-Pen†-NH$_2$ |
| (SEQ ID NO:120) | #53: | Mpr-K-G-D-W-P†-Pen-NH$_2$ |
| (SEQ ID NO:57) | #54: | Mpr-K-G-D↑-W-P-Pen-NH$_2$ |
| (SEQ ID NO:58) | #55: | Mpr-K-G-D-W-(Thz)-C-NH$_2$ |
| (SEQ ID NO:59) | #56: | Mpr-K-G-D-H(2,4-DNP)-P-C-NH$_2$ |
| (SEQ ID NO:60) | #57: | Mpr-K-G-D-(2-Nal)-P-Pen-NH$_2$ |
| (SEQ ID NO:61) | #58: | Mvl-K-G-D-W-P-Pen-NH$_2$ |
| (SEQ ID NO:62) | #59: | Mpr-K-G-D-W-(Pip)-Pen-NH$_2$ |
| (SEQ ID NO:63) | #60: | Mpr-(Har)-G-D-W-P-C-NH$_2$ |
| (SEQ ID NO:64) | #61: | Mpr-K-G-D-W-P-C†-NH$_2$ |
| (SEQ ID NO:65) | #62: | Mpr-(D-Lys)-G-D-W-P-Pen-NH$_2$ |
| (SEQ ID NO:66) | #63: | Mpr-(Har)-G-D-W-P-Pen-NH$_2$ |
| (SEQ ID NO:67) | #64: | Mpr-(Acetimidyl-Lys)-G-D-W-P-C-NH$_2$ |
| (SEQ ID NO:68) | #65: | Mpr-(Acetimidyl-Lys)-G-D-W-P-Pen-NH$_2$ |
| (SEQ ID NO:69) | #66: | Mpr-(N$^G$, N$^{G'}$-ethylene-Har)-G-D-W-P-C-NH$_2$ |
| (SEQ ID NO:70) | #67: | Mpr-(N$^G$, N$^{G'}$-ethylene-Har)-G-D-W-P-Pen-NH$_2$ |
| (SEQ ID NO:71) | #68: | Mpr-Har-Sar-G-D-W-P-C-NH$_2$ |
| (SEQ ID NO:72) | #69: | Mpr-(Acetimidyl-Lys)-G-D-W-P-Pen-NH$_2$ |
| (SEQ ID NO:73) | #70: | Mpr-(Phenylimidyl-Lys)-G-D-W-P-C-NH$_2$ |
| (SEQ ID NO:74) | #71: | Mpr-Har-Sar-D-W-P-Pen-NH$_2$ |
| (SEQ ID NO:75) | #72: | Mpr-(Phenylimidyl-Lys)-G-D-W-P-Pen-NH$_2$ |
| (SEQ ID NO:76) | #73: | Mpr-Har-G-D-W-(3,4-dehydro P)-C-NH$_2$ |

Example 8

PAI Activity of Peptides

When tested in the standard aggregation inhibition assays described above, analogs #3–5 had IC$_{50}$ values of 5 uM for ability to inhibit ADP-induced human platelet aggregation. However, analog #6 has an IC$_{50}$ of more than 200 uM, and analog #7, 100 uM. IC$_{50}$ values for the analogs of the invention in this essay are as follows:

| | Analog | Sequence | Appr. IC$_{50}$ (uM) |
|---|---|---|---|
| (SEQ ID NO:17) | #3 | G-C-G-K-G-D-W-P-C-A-NH$_2$ | 5 |
| (SEQ ID NO:18) | #4 | G-C-K-G-D-W-P-C-A-NH$_2$ | 5 |
| (SEQ ID NO:19) | #5 | C-G-K-G-D-W-P-C-NH$_2$ | 5 |
| (SEQ ID NO:110) | #6 | G-C-G-K-G-D-W-C-A-NH$_2$ | >200 |
| (SEQ ID NO:20) | #7 | G-C-K-G-D-W-C-A-NH$_2$ | 100 |
| (SEQ ID NO:111) | #8 | Acetyl-C-K-G-D-C-NH$_2$ | 200 |
| (SEQ ID NO:21) | #9 | Mpr-K-G-D-Pen-NH$_2$ | 25 |
| (SEQ ID NO:22) | #10 | C-K-G-D-W-P-C-NH$_2$ | 5 |
| (SEQ ID NO:112) | #11 | Acetyl-C-R-G-D-Pen-NH$_2$ | 5 |
| (SEQ ID NO:23) | #12 | C-K-G-D-Y-P-C-NH$_2$ | 12 |
| (SEQ ID NO:24) | #13 | C-K-G-D-F-P-C-NH$_2$ | 20 |
| (SEQ ID NO:30) | #19 | Mpr-K-G-D-W-P-C-NH$_2$ | 1 |
| (SEQ ID NO:45) | #34 | C-K-G-D-W-G-C-NH$_2$ | 100 |
| (SEQ ID NO:113) | #35 | C-K-G-E-W-P-C-NH$_2$ | >300 |
| (SEQ ID NO:114) | #36 | C-Orn-G-D-W-P-C-NH$_2$ | 150–200 |
| (SEQ ID NO:46) | #37 | C-K-A-D-W-P-C-NH$_2$ | 100 |
| (SEQ ID NO:115) | #38 | C-K-A†-D-W-P-C-NH$_2$ | >200 |
| (SEQ ID NO:47) | #39 | C-K-G-D-W-(Sar)-C-NH$_2$ | 5 |
| (SEQ ID NO:116) | #40 | C-K(Formyl)-G-D-W-P-C-NH$_2$ | >200 |
| (SEQ ID NO:48) | #41 | C-K-G-D-I-P-C-NH$_2$ | 100 |
| (SEQ ID NO:49) | #42 | C-K-G-D-(4-Cl-Phe)-P-NH$_2$ | 20 |
| (SEQ ID NO:50) | #43 | C-K-(Sar)-D-W-P-C-NH$_2$ | 50 |
| (SEQ ID NO:51) | #44 | C-K-G-D-(4-NO$_2$-Phe)-P-C-NH$_2$ | 75 |
| (SEQ ID NO:117) | #45 | C-K-G-D-(NMePhe)-P-C-NH$_2$ | >200 |
| (SEQ ID NO:118) | #46 | C-H-G-D-W-P-C-NH$_2$ | 200 |
| (SEQ ID NO:52) | #47 | Acetyl-C-K-G-D-W-P-C-NH$_2$ | 2.5 |
| (SEQ ID NO:53) | #48 | Mpr-K-G-D-W(Formyl)-P-C-NH$_2$ | 1 |
| (SEQ ID NO:54) | #49 | Mvl-K-G-D-W-P-C-NH$_2$ | 1.5 |
| (SEQ ID NO:119) | #50 | Mpr-K-G-D-W†-P-Pen-NH$_2$ | >200 |
| (SEQ ID NO:55) | #51 | Mpr-K-G-D-W-P-Pen-NH$_2$ | 0.75 |
| (SEQ ID NO:56) | #52 | Mpr-K-G-D-W-P-Pen†-NH$_2$ | 5 |
| (SEQ ID NO:120) | #53 | Mpr-K-G-D-W-P†-Pen-NH$_2$ | >200 |
| (SEQ ID NO:57) | #54 | Mpr-K-G-D†-W-P-Pen-NH$_2$ | >100 |
| (SEQ ID NO:58) | #55 | Mpr-K-G-D-W-(Thz)-C-NH$_2$ | 2 |
| (SEQ ID NO:59) | #56 | Mpr-K-G-D-H(2,4-DNP)-P-C-NH$_2$ | 5 |
| (SEQ ID NO:60) | #57 | Mpr-K-H-D-(2-Nal)-P-Pen-NH$_2$ | 1 |
| (SEQ ID NO:61) | #58 | Mvl-K-G-D-W-P-Pen-NH$_2$ | 1 |
| (SEQ ID NO:62) | #59 | Mpr-K-G-D-W-(Pip)-Pen-NH$_2$ | 1 |
| (SEQ ID NO:63) | #60 | Mpr-(Har)-G-D-W-P-C-NH$_2$ | 0.15 |
| (SEQ ID NO:64) | #61 | Mpr-K-G-D-W-P-C†-NH$_2$ | 15 |
| (SEQ ID NO:65) | #62 | Mpr-K†-G-D-W-P-Pen-NH$_2$ | 2.5 |
| (SEQ ID NO:66) | #63 | Mpr-(Har)-G-D-W-P-Pen-NH$_2$ | 0.10 |
| (SEQ ID NO:67) | #64 | Mpr-(Acetimidyl-Lys)-G-D-W-P-C-NH$_2$ | 0.25 |
| (SEQ ID NO:71) | #68 | Mpr-Har-Sar-D-W-P-C-NH$_2$ | 3.0 |
| (SEQ ID NO:72) | #69 | Mpr-(Acetimidyl-Lys)-G-D-W-P-Pen-NH$_2$ | 0.5 |
| (SEQ ID NO:73) | #70 | Mpr-(Phenylimidyl-Lys)-G-D-W-P-C-NH$_2$ | 0.5 |
| (SEQ ID NO:74) | #71 | Mpr-Har-Sar-D-W-P-Pen-NH$_2$ | 2.5 |
| (SEQ ID NO:75) | #72 | Mpr-(Phenylimidyl-Lys)-G-D-W-P-Pen-NH$_2$ | 0.5 |

Example 9

Activity of Linear versus Cyclic Peptides

When tested for inhibition of fibrinogen binding to GP IIb-IIIa in the plate assay, linear (SEQ ID NO:104) RGDW-NH$_2$ was very similar in activity to cyclic (SEQ ID NO:105) GCGRGDWPCA-NH$_2$. In contrast, the linear (SEQ ID NO:106) KGDW-NH$_2$ was much less potent than cyclic (SEQ ID NO:107) GCGKGDWPCA-NH$_2$. For the KGDW compounds, but not the RGDW compounds, cyclization resulted in a marked increase in the ability of the peptide to inhibit the binding of fibrinogen to GP IIb-IIIa.

Example 10

Results of Plate Binding Assays for Synthetic Peptides

The peptides synthesized in Example 8, in addition to being assessed for the ability to inhibit platelet aggregation directly, were also tested in the plate assays as described above and indicated that these analogs are differentially capable, to varying degrees, of inhibiting the binding of fibrinogen to GP IIb-IIIa as compared to vitronectin to vitronectin receptor. Analog #4 appears, among this group, to have the highest differential. Analogs #7 and #5, on the other hand, are also quite specific, and have excellent platelet aggregation inhibition activities.

Example 11

Effects of Purified Peptides on Cell Adhesion

M21 melanoma cells were labelled with $^{35}$S-methionine, and then added to vitronectin-coated plates in the presence of the indicated concentrations of purified snake venom peptides. Cell attachment was measured by solubilizing the cells remaining after an incubation and wash, as previously describe. Neither barbourin nor Peptide 1 (truncated barbourin) had a significant effect on cell adhesion to vitronectin, although both are potent inhibitors of platelet aggregation. In contrast, cotiarin, which is a potent inhibitor of vitronectin binding to the vitronectin receptor, was very potent in inhibiting cell attachment to vitronectin. In similar experiment, Peptide #3. Peptide #3 with K replaced by R (SEQ ID NO:105) (GCGRGDWPCA-NH$_2$) and (SEQ ID NO:108) RGDS were examined on M21 cell attachment to vitronectin. (SEQ ID NO:108) RGDS and (SEQ ID NO:105) GCGRGDWPCA-NH$_2$ are potent inhibitors of cell attachment whereas (SEQ ID NO:107) GCGKGDWPCA-NH$_2$ was ineffective up to 60 uM.

Example 12

Comparison of Analogs 60 and 19

Analogs 60 and 19 described above containing the sequence (SEQ ID NO:12) K*GDX and are identical except for the embodiment of K*. Analog 60 is of the formula:

(SEQ ID NO:63) Mpr-(Har)-G-D-W-P-C-NH2;

analog 19 is of the formula:

(SEQ ID NO:30) Mpr-K-G-D-W-P-C-NH2.

These analogs were tested by standard platelet aggregation inhibition assays and using the cell adhesion assay of Example 11 above. Analog #60 was efficient at vanishingly small concentrations in inhibiting platelet aggregation, and was relatively less effective in preventing cell adhesion to vitronectin. Analog #19 had good platelet aggregation inhibition activity as well as specificity; however, it was less active in the platelet aggregation inhibition assay than its analog #60 counterpart. Analog #60 had an IC$_{50}$ in platelet aggregation of approximately 0.15 nM; analog #19 had an IC$_{50}$ of approximately 1 nM.

Example 13

Construction of Expression Vectors for Barbourin Peptides

A gene encoding the full length [L$^{41}$] barbourin peptide (1–73) was assembled from synthetic oligonucleotides as shown in FIG. 38 of WO 90/15620, which were kinased, annealed and ligated into EcoRI-HindIII digested M13mp18 using standard procedures. The bacterial alkaline phosphatase gene (phoA) signal sequence (Watson, M. E. E., *Nucleic Acids Research* (1984) 12:5145) was added to the barbourin construct by ligating synthetic oligonucleotides into the EcoRI/NcoI sites of the [L$^{41}$] barbourin (1–73) construct as shown in FIG. 39 of WO 90/15620. The nucleotide sequences of all constructs were verified by the Sanger dideoxy chain termination method.

A truncated version of this peptide was also constructed from synthetic oligonucleotides which would encode only amino acids 28–73 of the full length molecule. Two alterations, Q$^{28}$ to E$^{28}$ and A$^{64}$ to C$^{64}$ were introduced using site directed mutagenesis as described by Kunkel et al. *Meth Enzymol* (1987) 154:367. The phoA signal sequence was added to the truncated version as described above (FIG. 40 of WO 90/15620). In addition, the signal sequence for the *E. coli* heat-stable enterotoxin II (Picken, R. W., et al. *Infect Immun* (1983) 42:269) was added to the truncated version using synthetic oligonucleotides with EcoRI and NcoI compatible ends. All bacterial secretion constructs were subcloned into the bacterial expression vector pPROK-1 (Brosius, J., *Gene* (1984) 27:151, ibid:161), available commercially from CLONTECH Lab, Inc. using EcoRI and HindIII restriction endonucleases.

A gene encoding tandem repeats of the desired title peptide was prepared using the polymerase chain reaction (PCR) to produce the multimerization unit from the full-length barbourin peptide 1–73 containing L41 and C64.

FIG. 41 of WO 90/15620 shows the oligonucleotides used for the PCR synthesis. The PCR reaction was conducted according to the method of Saki, R. K., et al. *Science* (1988) 239:487. The resulting polymer junction contains methionines at either end of the sequence as shown in WO 90/15620, FIG. 42, and provides desirable restriction sites for the construct.

The tandem repeats are formed from the individual multimer-forming components by, for example, ligating an EcoRI/BamHI fragment to a BglII/HindIII fragment in an M13mp18 vector cut with EcoRI/HindIII to form a dimer. The resultant dimer is excised with EcoRI and BamHI and relegated to a BglII/HindIII fragment to produce a trimer, and so on until the desired size is obtained. This construction is diagramed in FIG. 43 of WO 90/15620.

The multimer was then ligated into the *E. coli* vector pKK233-2, Amann, E., et al., *Gene* (1985) 40:183, available from Clontech, by digesting the vector with NcoI/HindIII and ligating a monomer subfragment of NcoI/BamHI and multimer subfragments of BglII/HindIII.

For expression as a fusion protein, the above digested vector was used along with an NcoI/EcoRI subfragment containing a slightly modified amino-terminal portion (amino acids 1 to 72) of the chloramphenicol acetyltransferase gene (Chang, C. N., et al., *Gene* (1987) 55:189) and EcoRI-HindIII subfragments of the multimer constructions.

Example 14

Expression of Recombinant Genes

Protein expression from all of the recombinant plasmids described above is induced according to Kanamari et al., *Gene* (1988) 66:295 after transfection into appropriate *E. coli* host strains. Products are characterized by sodium dodecyl sulfate polyacrylamide gel electrophoresis and by their ability to inhibit ADP-induced platelet aggregation in platelet-rich plasma. Following purification, the multimeric proteins are converted to monomer units with cyanogen bromide cleavage and the products assayed as above.

Example 15

Preparation of Additional Analogs

The following analogs were synthesized in a manner similar to that set forth in Example 6 and were tested for PAI activity in the assay method described hereinabove.

| | Analog | Sequence | Appr.IC$_{20}$ (μM) |
|---|---|---|---|
| (SEQ ID NO:79) | PAI 80 | Mpr-P-Har-G-D-W-P-C-NH$_2$ | 1.29 |
| (SEQ ID NO:80) | PAI 81 | Mpr-G-Har-G-D-W-P-C-NH$_2$ | 7.47 |
| (SEQ ID NO:81) | PAI 82 | Mpr-A-Har-G-D-W-P-C-NH$_2$ | 0.12 |
| (SEQ ID NO:82) | PAI 83 | Mpr-Aib-Har-G-D-W-P-C-NH$_2$ | 2.20 |
| (SEQ ID NO:83) | PAI 84 | Mpr-(N-Me-Arg)-Har-G-D-W-P-C-NH$_2$ | 0.25 |
| (SEQ ID NO:84) | PAI 85 | Mpr-(N-Me-Sar)-Har-G-D-W-P-C-NH$_2$ | 0.28 |
| (SEQ ID NO:85) | PAI 86 | Mpr-A†-Har-G-D-W-P-C-NH2 | 1.15 |
| (SEQ ID NO:86) | PAI 87 | Mpr-(β-Ala)-Har-G-D-W-P-C-NH2 | 0.92 |

-continued

| | Analog | Sequence | Appr.IC$_{20}$ (μM) |
|---|---|---|---|
| (SEQ ID NO:87) | PAI 88 | Mpr-(N-Me-Leu)-Har-G-D-W-P-C-NH2 | 0.84 |
| (SEQ ID NO:88) | PAI 89 | Mpr-(N-Me-Ala)-Har-G-D-W-P-C-NH2 | 0.62 |
| (SEQ ID NO:89) | PAI 90 | Mpr-Sar-Har-G-D-W-P-C-NH2 | 0.27 |
| (SEQ ID NO:90) | PAI 91 | Mpr-V-Har-G-D-W-P-C-NH2 | 0.35 |
| (SEQ ID NO:91) | PAI 92 | Mpr-S-Har-G-D-W-P-C-NH2 | 0.24 |
| (SEQ ID NO:92) | PAI 93 | Mpr-Har-G-D-W-P-A-C-NH2 | 3.33 |
| (SEQ ID NO:93) | PAI 94 | Mpr-Har-G-D-W-P-(N-Me-Ala)-C-NH2 | 1.46 |
| (SEQ ID NO:94) | PAI 95 | Mpr-Har-G-D-W-P-G-C-NH2 | 8.66 |
| (SEQ ID NO:95) | PAI 96 | Mpr-Har-G-D-W-P-A†-C-NH2 | 0.23 |
| (SEQ ID NO:96) | PAI 97 | Mpr-Har-G-D-W-P-P-C-NH2 | 1.40 |
| (SEQ ID NO:97) | PAI 98 | Mpr-Har-G-D-W-P-(Sar)-C-NH$_2$ | 0.31 |
| (SEQ ID NO:98) | PAI 99 | Mpr-Har-G-D-W-P-(Aib)-NH2 | 0.46 |
| (SEQ ID NO:99) | PAI 100 | Mpr-A-(Har)-G-D-W-P-Pen-NH2 | 0.37 |
| (SEQ ID NO:100) | PAI 101 | Mpr-A-K-G-D-W-P-Pen-NH2 | 4.91 |
| (SEQ ID NO:101) | PAI 102 | Mpr-D-(Har)-G-D-W-P-Pen-NH2 | 4.04 |

Example 16

Stability Determination

A solution was formed in 1.0M citric acid of greater than 95% pure cyclic form of SEQ ID NO:63) Mpr-(L-homoarginine)-Gly-Asp-Trp-Pro-Cys-NH2•acetate polypeptide (I) at a concentration of up to 200 mg per ml of solution. This solution was diluted to the desired final peptide concentration as follows: This solution was first diluted to about 85% of the final volume with water. The pH of the solution was adjusted to 5.0–5.5 using sodium hydroxide. The solution was then diluted to the final volume with water. Compositions having a concentration of (I) of 0.5 mg/ml and 5.0 mg/ml were formulated and evaluated for stability by HPLC, UV and visual inspection as described in Example 1. The compositions were also evaluated for platelet aggregation inhibiting activity using the assay described above. Results of these experiments are set forth in Tables 4 and 5 below.

TABLE 4

Stability of 0.5 mg/ml Composition

| Temp (°C.) | Time (Days) | CAC[a] | pH | HPLC[b] (% Area) | HPLC (mg/mL) | UV (mg/mL) | Activity[c] (nM) |
|---|---|---|---|---|---|---|---|
| 5 | 0 | CC | 5.44 | 98.6 | 0.51 | 0.50 | 175 |
| 5 | 32 | CC | 5.45 | 98.8 | 0.50 | 0.49 | 183 |
| -15 | 32 | CC | 5.46 | 98.9 | 0.50 | 0.50 | 199 |
| 30 | 32 | CC | 5.44 | 98.4 | 0.50 | 0.50 | 174 |
| 45 | 32 | CC | 5.44 | 97.1 | 0.50 | 0.50 | 202 |

[a]CC = Clear, colorless solution; CvPY = Clear, very pale yellow solution;
[b]Purity expressed as a percent of total peak area.
[c]Activity expressed as an IC$_{50}$ (the concentration calculated to achieve a 50% inhibition of platelet aggregation).

TABLE 5

Stability of 5 mg/ml Composition

| Temp (°C.) | Time (Days) | CAC[a] | pH | HPLC[b] (% Area) | HPLC (mg/mL) | UV (mg/mL) | Activity[c] (nM) |
|---|---|---|---|---|---|---|---|
| 5 | 0 | CC | 5.39 | 99.5 | 5.30 | 5.04 | 88 |
| 5 | 29 | CC | 5.40 | 98.3 | 5.35 | NT | NT |
| 5 | 60 | CC | 5.40 | 98.3 | 4.71 | NT | NT |
| 5 | 90 | CC | 5.38 | 97.9 | 4.97 | NT | NT |
| 30 | 29 | CC | 5.41 | 98.4 | 4.76 | NT | NT |
| 30 | 60 | CC | 5.40 | 97.4 | 4.64 | NT | NT |
| 30 | 90 | CC | 5.39 | 96.9 | 4.87 | NT | NT |
| 45 | 29 | CC | 5.41 | 96.4 | 4.65 | NT | NT |
| 45 | 69 | CC | 5.41 | 93.9 | 4.22 | NT | NT |
| 45 | 90 | CvPY | 5.39 | 89.8 | 4.14 | NT | NT |

[a]CC = Clear, colorless solution; CvPY = Clear, very pale yellow solution;
[b]Purity expressed as a percent of total peak area.
[c]Activity expressed as an IC$_{50}$ (the concentration calculated to achieve a 50% inhibition of platelet aggregation).
NT No testing required at this timepoint.

Results of these experiments set forth in Tables 4 and 5 demonstrated that the liquid solutions of the polypeptide of the invention having a pH of 5.0–5.5 were very stable from about −15° C. to about 45° C. The compositions were also found to be normal on visual inspection.

What is claimed is:

1. A method of storage-stabilizing a substantially pure platelet aggregation inhibitor (PAI) polypeptide comprising preparing a liquid solution consisting essentially of said polypeptide in a citrate buffer by dissolving said polypeptide in said citrate buffer to form a storage-stable solution having a pH of from about 5.0 to about 5.5.

2. A method according to claim 1 wherein said polypeptide has the formula

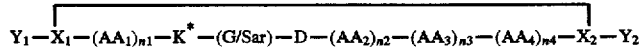

$$Y_1 - X_1 - (AA_1)_{n1} - K^* - (G/Sar) - D - (AA_2)_{n2} - (AA_3)_{n3} - (AA_4)_{n4} - X_2 - Y_2$$

wherein K* has the formula

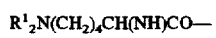

$$R^1_2 N(CH_2)_4 CH(NH) CO-$$

wherein (G/Sar) is selected from the group consisting of G and Sar;

wherein each $R^1$ is independently H, alkyl (1–6 C), or at most one $R^1$ is $R^2-C=NR^3$, wherein $R^2$ is H, alkyl (1–6 C) or is a substituted or unsubstituted phenyl or benzyl residue, or is $NR^4_2$ in which each $R^4$ is independently H or alkyl (1–6 C), and $R^3$ is H, alkyl (1–6 C), phenyl or benzyl, or $R^2-C=NR^3$ is a radical selected from the group consisting of

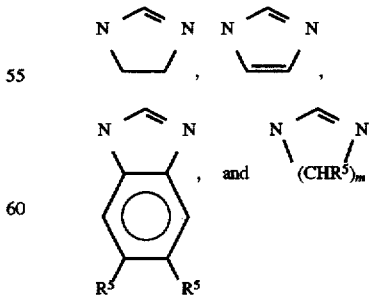

where m is an integer of 2–3, and each $R^5$ is independently H or alkyl (1–6 C);

and where one or two (CH$_2$) is optionally replaced by O or S provided said O or S is not adjacent to another heteroatom;

AA$_1$, is a small, neutral (polar or nonpolar) amino acid and n1 is an integer of 0–3;

AA$_2$ is a neutral, nonpolar large (aromatic or nonaromatic) or a polar aromatic amino acid and n2 is an integer of 0–3;

AA$_3$ is a proline residue or a modified proline residue of the formula

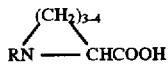
RN——CHCOOH wherein one or two of the methylenes of said proline or modified proline residue is optionally replaced by —NR—, —S—, or —O— wherein R is hydrogen or alkyl (1–6 C) and n3 is an integer of 0–1;

AA$_4$ is a neutral, small amino acid or the N-alkylated form thereof and n4 is an integer of 0–3;

each of X$_1$, and X$_2$ is independently a residue capable of forming a bond between X$_1$, and X$_2$ to obtain a cyclic compound as shown; and each of Y$_1$ and Y$_2$ is independently a noninterfering substituent or is absent;

wherein one or more peptide linkages may optionally be replaced by linkage selected from the group consisting of —CH$_2$NH—, —CH$_2$S—, —CH$_2$CH$_2$—, —CH=CH— (cis and trans), —COCH$_2$—, —CH(OH)CH$_2$— and —CH$_2$SO—.

3. The method of claim 2 wherein said Y$_1$ is H, acyl, or a peptide residue or derivatized form thereof or is absent and Y$_2$ is OH, NH$_2$, —A—NH$_2$ or a peptide residue or derivatized form thereof or is absent, X$_1$ and X$_2$ are selected from the group consisting of cysteine (C), mercaptovaleryl (Mvl), mercaptoproprionyl (Mpr) and penicillamine (Pen), AA$_1$, is G and n1 is 0 or 1, AA$_2$ is selected from the group consisting of W, F, L, Y, and V and K* is K, Har, acetimidyl-Lys or phenylimidyl-Lys.

4. The method of claim 3 wherein the polypeptide is selected from the group consisting

| | |
|---|---|
| (SEQ ID NO:53) | Mpr-K-G-D-W(Formyl)-P-C-NH$_2$ |
| (SEQ ID NO:54) | Mvl-K-G-D-W-P-C-NH$_2$ |
| (SEQ ID NO:55) | Mpr-K-G-D-W-P-Pen-NH$_2$ |
| (SEQ ID NO:63) | Mpr-(Har)-G-D-W-P-C-NH$_2$ |
| (SEQ ID NO:66) | Mpr-(Har)-G-D-W-P-Pen-NH$_2$ |
| (SEQ ID NO:67) | Mpr(Acetimidyl-Lys)-G-D-W-P-C-NH$_2$ |
| (SEQ ID NO:68) | Mpr(Acetimidyl-Lys)-G-D-W-P-Pen-NH$_2$ |
| (SEQ ID NO:73) | Mpr(Phenylimidyl-Lys)-G-D-W-P-C-NH$_2$ |
| (SEQ ID NO:75) | Mpr(Phenylimidyl-Lys)-G-D-W-P-Pen-NH$_2$ |
| (SEQ ID NO:81) | Mpr-Ala-(Har)-G-D-W-P-C-NH$_2$ |
| | [Mpr-L-homoarginine-G-D-W-P-C-NH$_2$] and |
| (SEQ ID NO:30) | Mpr-K-G-D-W-P-C-NH$_2$ |

5. A method according to claim 2 wherein said solution is stable at about 70° C. for at least 49 days.

6. The method according to claim 1 wherein said polypeptide is biologically active for inhibiting thrombus formation, preventing platelet loss during extracorporeal circulation of blood or for treating a patient suspected of having a platelet-associated ischemic syndrome.

7. The method according to claim 1 wherein the pH is about 5.25.

8. The method according to claim 7 wherein the stabilizing is at about −15° C. to about 30° C.

9. The method according to claim 1 wherein the stability is at about 5 to about 30° C.

10. The method according to claim 1 wherein said polypeptide is a cyclic polypeptide containing up to 10 amino acid residues and is stabilized in a solution having a pH of about 5.25, in which the citrate buffer solution includes sodium hydroxide.

11. A storage-stable composition comprising a substantially pure platelet aggregation inhibitor polypeptide dissolved in a liquid solution in which additives that provide storage stability consist essentially of a stabilizing effective amount of a citrate buffer, said composition having a pH of from about 5.0 to about 5.5.

12. A storage-stable composition according to claim 11, wherein said polypeptide has the formula

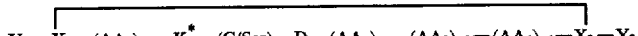

Y$_1$—X$_1$—(AA$_1$)$_{n1}$—K*—(G/Sar)—D—(AA$_2$)$_{n2}$—(AA$_3$)$_{n3}$—(AA$_4$)$_{n4}$—X$_2$—Y$_2$ wherein K* has the formula

R$^1_2$N(CH$_2$)$_4$CH(NH)CO— wherein (G/Sar) is selected from the group consisting of G and Sar;

wherein each R$^1$ is independently H, alkyl(1–6 C), or at most one R$^1$ is R$^2$—C=NR$^3$, wherein R$^2$ is H, alkyl or is a substituted or unsubstituted phenyl or benzyl residue, or is NR$^4_2$ in which each R$^4$ is independently H or alkyl(1–6 C), and R$^3$ is H, alkyl(1–6 C), phenyl or benzyl, or R$^2$—C=NR$^3$ is a radical selected from the group consisting of

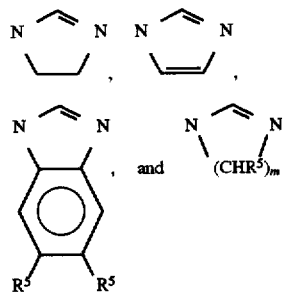

where m is an integer of 2–3, and each R$^5$ is independently H or alkyl (1–6 C);

and wherein one or two (CH$_2$) is optionally replaced by O or S provided said O or S is not adjacent to another heteroatom;

AA$_1$, is a small, neutral (polar or nonpolar) amino acid and n1 is an integer of 0–3;

AA$_2$ is a neutral, nonpolar large (aromatic or nonaromatic) or a polar aromatic amino acid and n2 is an integer of 0–3;

AA$_3$ is a proline residue or a modified proline residue of the formula

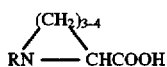

wherein one or two of the methylenes of said proline or modified proline residue is optionally replaced by —NR—, —S—, or —O— wherein R is hydrogen or alkyl (1–6 C) and n3 is an integer of 0–1;

AA$_4$ is a neutral, small amino acid of the N-alkylated form thereof and n4 is an integer of 0–3;

each of X$_1$ and X$_2$ is independently a residue capable of forming a bond between X$_1$ and X$_2$ to obtain a cyclic compound as shown; and each of Y$_1$ and Y$_2$ is independently a noninterfering substituent or is absent;

wherein one or more peptide linkages is optionally be replaced by a linkage selected from the group consisting of —CH$_2$NH—, —CH$_2$S—, —CH$_2$CH$_2$—, —CH=CH— (cis and trans), —COCH$_2$—, —CH(OH)CH$_2$— and —CH$_2$SO—.

13. The composition of claim 12 wherein said Y$_1$ is H, acyl, or a peptide residue or derivatized form thereof or is absent and Y$_2$ is OH, NH$_2$, —A—NH$_2$ or a peptide residue or derivatized form thereof or is absent, X$_1$ and X$_2$ are selected from the group consisting of cysteine (C), mercaptovaleryl (Mvl), mercaptoproprionyl (Mpr) and penicillamine (Pen), AA$_1$ is G and n1 is 0 or 1, AA$_2$ is selected from the group consisting of W, F, L, Y, and V and K* is K, Har, acetimdyl-Lys or phenylimidyl-Lys.

14. The composition of claim 12 wherein the polypeptide is selected from the group consisting of

| (SEQ ID NO:53) | Mpr-K-G-D-W(Formyl)-P-C-NH$_2$ |
| (SEQ ID NO:54) | Mvl-K-G-D-W-P-C-NH$_2$ |
| (SEQ ID NO:55) | Mpr-K-G-D-W-P-Pen-NH$_2$ |
| (SEQ ID NO:63) | Mpr-(Har)-G-D-W-P-C-NH$_2$ |
| (SEQ ID NO:66) | Mpr-(Har)-G-D-W-P-Pen-NH$_2$ |
| (SEQ ID NO:67) | Mpr(Acetimidyl-Lys)-G-D-W-P-C-NH$_2$ |
| (SEQ ID NO:68) | Mpr(Acetimidyl-Lys)-G-D-W-P-Pen-NH$_2$ |
| (SEQ ID NO:73) | Mpr(Phenylimidyl-Lys)-G-D-W-P-C-NH$_2$ |
| (SEQ ID NO:75) | Mpr(Phenylimidyl-Lys)-G-D-W-P-Pen-NH$_2$ |
| (SEQ ID NO:81) | Mpr-Ala-(Har)-G-D-W-P-C-NH$_2$ [Mpr-L-homoarginine-G-D-W-P-C-NH$_2$] and |
| (SEQ ID NO:30) | Mpr-K-G-D-W-P-C-NH$_2$. |

15. A composition of claim 12 stabilized at about 70° C. or less for at least 49 days.

16. A storage-stable therapeutic liquid composition comprising an injectable, biologically effective amount of a substantially pure platelet aggregation inhibitor polypeptide dissolved in a liquid solution in which additives that provide storage stability consist essentially of a citrate buffer, said solution having a pH of from about 5.0 to about 5.5.

17. The liquid composition according to claim 16 wherein said polypeptide is biologically active for inhibiting thrombus formation, preventing platelet loss during extracorporeal circulation of blood or for treating a patient suspected of having a platelet-associated ischemic syndrome.

18. The composition according to claim 16 wherein said pH is about 5.25.

19. The liquid composition according to claim 16 wherein said polypeptide is a cyclic polypeptide containing up to 10 amino acid residues and is stabilized in a solution having a pH of about 5.25, in which the citrate buffer solution includes sodium hydroxide.

20. An article of manufacture comprising a sterile delivery vial, bag or bottle filled with a liquid composition of claim 16 in injectable form.

* * * * *

SEQUENCE LISTING ( 1 ) GENERAL INFORMATION:

( i i i ) NUMBER OF SEQUENCES: 120

( 2 ) INFORMATION FOR SEQ ID NO:1:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or mercaptopropionyl."

( i x ) FEATURE:
( A ) NAME/KEY: Modified-site
( B ) LOCATION: 5
( D ) OTHER INFORMATION: /note="This position is Trp(Formyl)."

( i x ) FEATURE:
  ( A ) NAME/KEY: Modified-site
  ( B ) LOCATION: 7
  ( D ) OTHER INFORMATION: /note="This position is Cys-NH2."

( x i ) SEQUENCE DESCRIPTION: SEQ ID NO:1:

Xaa Lys Gly Asp Xaa Pro Cys
1        5

( 2 ) INFORMATION FOR SEQ ID NO:2:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is mvl or mercaptovaleryl."

( i x ) FEATURE:
  ( A ) NAME/KEY: Modified-site
  ( B ) LOCATION: 7
  ( D ) OTHER INFORMATION: /note="This position is Cys-NH2."

( x i ) SEQUENCE DESCRIPTION: SEQ ID NO:2:

Xaa Lys Gly Asp Trp Pro Cys
1        5

( 2 ) INFORMATION FOR SEQ ID NO:3:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is Mpr or mercaptopropionyl."

( i x ) FEATURE:
  ( A ) NAME/KEY: Modified-site
  ( B ) LOCATION: 7
  ( D ) OTHER INFORMATION: /note="This position is Pen-NH2."

( x i ) SEQUENCE DESCRIPTION: SEQ ID NO:3:

Xaa Lys Gly Asp Trp Pro Xaa
1        5

( 2 ) INFORMATION FOR SEQ ID NO:4:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is Mpr or mercaptopropionyl."

( i x ) FEATURE:
  ( A ) NAME/KEY: Modified-site
  ( B ) LOCATION: 2

(D) OTHER INFORMATION: /note="This position is
(Acetimidyl-Lys)."

(ix) FEATURE:
    (A) NAME/KEY: Modified-site
    (B) LOCATION: 7
    (D) OTHER INFORMATION: /note="This position is Cys-NH2."

(xi) SEQUENCE DESCRIPTION: SEQ ID NO:4:

Xaa Xaa Gly Asp Trp Pro Cys
1                  5

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr or
            mercaptopropionyl."

(ix) FEATURE:
        (A) NAME/KEY: Modified-site
        (B) LOCATION: 2
        (D) OTHER INFORMATION: /note="This position is
        (Acetimidyl-Lys)."

(ix) FEATURE:
        (A) NAME/KEY: Modified-site
        (B) LOCATION: 7
        (D) OTHER INFORMATION: /note="This position is Pen-NH2."

(xi) SEQUENCE DESCRIPTION: SEQ ID NO:5:

Xaa Xaa Gly Asp Trp Pro Xaa
1                  5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr or
            mercaptopropionyl."

(ix) FEATURE:
        (A) NAME/KEY: Modified-site
        (B) LOCATION: 2
        (D) OTHER INFORMATION: /note="This position is
        (Phenylimidyl-Lys)."

(ix) FEATURE:
        (A) NAME/KEY: Modified-site
        (B) LOCATION: 7
        (D) OTHER INFORMATION: /note="This position is Cys-NH2."

(xi) SEQUENCE DESCRIPTION: SEQ ID NO:6:

Xaa Xaa Gly Asp Trp Pro Cys
1                  5

(2) INFORMATION FOR SEQ ID NO:7:

(i) SEQUENCE CHARACTERISTICS:
        (A) LENGTH: 7 amino acids (B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is (Phenylimidyl-Lys)."

(ix) FEATURE:
(A) NAME/KEY: Modified-site
(B) LOCATION: 7
(D) OTHER INFORMATION: /note="This position is Pen-NH2."

(xi) SEQUENCE DESCRIPTION: SEQ ID NO:7:

Xaa Xaa Gly Asp Trp Pro Xaa
1               5

(2) INFORMATION FOR SEQ ID NO:8:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 3
(D) OTHER INFORMATION: /note="This position is (Har or homoarginine)."

(ix) FEATURE:
(A) NAME/KEY: Modified-site
(B) LOCATION: 8
(D) OTHER INFORMATION: /note="This position is Cys-NH2."

(xi) SEQUENCE DESCRIPTION: SEQ ID NO:8:

Xaa Ala Xaa Gly Asp Trp Pro Cys
1               5

(2) INFORMATION FOR SEQ ID NO:9:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is L-homoarginine."

(ix) FEATURE:
(A) NAME/KEY: Modified-site ( B ) LOCATION: 7
( D ) OTHER INFORMATION: /note="This position is Cys-NH2."

( x i ) SEQUENCE DESCRIPTION: SEQ ID NO:9:

Xaa Xaa Gly Asp Trp Pro Cys
1               5

( 2 ) INFORMATION FOR SEQ ID NO:10:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or mercaptopropionyl."

( i x ) FEATURE:
( A ) NAME/KEY: Modified-site
( B ) LOCATION: 7
( D ) OTHER INFORMATION: /note="This position is Cys-NH2."

( x i ) SEQUENCE DESCRIPTION: SEQ ID NO:10:

Xaa Lys Gly Asp Trp Pro Cys
1               5

( 2 ) INFORMATION FOR SEQ ID NO:11:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:11:

Arg Gly Asp Xaa
1

( 2 ) INFORMATION FOR SEQ ID NO:12:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is K* which is R12N(CH2)4CH(NH)CO-."

( x i ) SEQUENCE DESCRIPTION: SEQ ID NO:12:

Xaa Gly Asp Xaa
1

( 2 ) INFORMATION FOR SEQ ID NO:13:

( i ) SEQUENCE CHARACTERISTICS:
( A ) LENGTH: 46 amino acids
( B ) TYPE: amino acid
( C ) STRANDEDNESS: single
( D ) TOPOLOGY: linear ( x i ) SEQUENCE DESCRIPTION: SEQ ID NO:13:

Glu Cys Ala Asp Gly Leu Cys Cys Asp Gln Cys Arg Phe Leu Lys Lys
1               5                   10                  15

```
            Gly  Thr  Val  Cys  Arg  Val  Ala  Lys  Gly  Asp  Trp  Asn  Asp  Asp  Thr  Cys
                           20                      25                          30

Thr  Gly  Gln  Ser  Cys  Asp  Cys  Pro  Arg  Asn  Gly  Leu  Tyr  Gly
                           35                      40                      45
```

( 2 ) INFORMATION FOR SEQ ID NO:14:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
            Glu  Glu  Pro  Cys  Ala  Thr  Gly  Pro  Cys  Cys  Arg  Arg  Cys  Lys  Phe  Lys
            1                       5                      10                          15

Arg  Ala  Gly  Lys  Val  Cys  Arg  Val  Ala  Lys  Gly  Asp  Trp  Asn  Asn  Asp
                           20                      25                          30

Tyr  Cys  Thr  Gly  Lys  Ser  Cys  Asp  Cys  Pro  Arg  Asn  Pro  Trp  Asn  Gly
                           35                      40                      45
```

( 2 ) INFORMATION FOR SEQ ID NO:15:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
            Glu  Cys  Ala  Asp  Gly  Leu  Cys  Cys  Asp  Gln  Cys  Arg  Phe  Leu  Lys  Lys
            1                       5                      10                          15

Gly  Thr  Val  Cys  Arg  Val  Ala  Lys  Gly  Asp  Trp  Asn  Asp  Asp  Thr  Cys
                           20                      25                          30

Thr  Gly  Gln  Ser  Cys  Asp  Cys  Pro  Arg  Asn  Gly  Leu  Tyr  Gly
                           35                      40                      45
```

( 2 ) INFORMATION FOR SEQ ID NO:16:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
            Glu  Glu  Pro  Cys  Ala  Thr  Gly  Pro  Cys  Cys  Arg  Arg  Cys  Lys  Phe  Lys
            1                       5                      10                          15

Arg  Ala  Gly  Lys  Val  Cys  Arg  Val  Ala  Lys  Gly  Asp  Trp  Asn  Asn  Asp
                           20                      25                          30

Tyr  Cys  Thr  Gly  Lys  Ser  Cys  Asp  Cys  Pro  Arg  Asn  Pro  Trp  Asn  Gly
                           35                      40                      45
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 10
        ( D ) OTHER INFORMATION: /note="This position is A-NH2."

( x i ) SEQUENCE DESCRIPTION: SEQ ID NO:17:

Gly Cys Gly Lys Gly Asp Trp Pro Cys Xaa
1               5                           10

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 9
        ( D ) OTHER INFORMATION: /note="This position is A-NH2."

( x i ) SEQUENCE DESCRIPTION: SEQ ID NO:18:

Gly Cys Lys Gly Asp Trp Pro Cys Xaa
1               5

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 8
        ( D ) OTHER INFORMATION: /note="This position is C-NH2."

( x i ) SEQUENCE DESCRIPTION: SEQ ID NO:19:

Cys Gly Lys Gly Asp Trp Pro Xaa
1               5

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 7
        ( D ) OTHER INFORMATION: /note="This position is A-NH2."

( x i ) SEQUENCE DESCRIPTION: SEQ ID NO:20:

Cys Lys Gly Asp Trp Cys Xaa
1               5

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr or
            mercaptopropionyl."

( i x ) FEATURE:
        ( A ) NAME/KEY: Modified-site (B) LOCATION: 5
(D) OTHER INFORMATION: /note="This position is Pen-NH2."

(x i) SEQUENCE DESCRIPTION: SEQ ID NO:21:

Xaa Lys Gly Asp Xaa
1               5

(2) INFORMATION FOR SEQ ID NO:22:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 7
(D) OTHER INFORMATION: /note="This position is C-NH2."

(x i) SEQUENCE DESCRIPTION: SEQ ID NO:22:

Cys Lys Gly Asp Trp Pro Xaa
1               5

(2) INFORMATION FOR SEQ ID NO:23:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 7
(D) OTHER INFORMATION: /note="This position is C-NH2."

(x i) SEQUENCE DESCRIPTION: SEQ ID NO:23:

Cys Lys Gly Asp Tyr Pro Xaa
1               5

(2) INFORMATION FOR SEQ ID NO:24:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 7
(D) OTHER INFORMATION: /note="This position is C-NH2."

(x i) SEQUENCE DESCRIPTION: SEQ ID NO:24:

Cys Lys Gly Asp Phe Pro Xaa
1               5

(2) INFORMATION FOR SEQ ID NO:25:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 7
(D) OTHER INFORMATION: /note="This position is C-NH2."

(x i) SEQUENCE DESCRIPTION: SEQ ID NO:25:

Cys Lys Gly Asp Leu Pro Xaa
1               5

( 2 ) INFORMATION FOR SEQ ID NO:26:

( i ) SEQUENCE CHARACTERISTICS:
       ( A ) LENGTH: 7 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 7
       ( D ) OTHER INFORMATION: /note="This position is C-NH2."

( x i ) SEQUENCE DESCRIPTION: SEQ ID NO:26:

Cys Lys Gly Asp Val Pro Xaa
1               5

( 2 ) INFORMATION FOR SEQ ID NO:27:

( i ) SEQUENCE CHARACTERISTICS:
       ( A ) LENGTH: 7 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 5
       ( D ) OTHER INFORMATION: /note="This position is Y(OMe) or
             Tyr(OMe)."

( i x ) FEATURE:
       ( A ) NAME/KEY: Modified-site
       ( B ) LOCATION: 7
       ( D ) OTHER INFORMATION: /note="This position is C-NH2."

( x i ) SEQUENCE DESCRIPTION: SEQ ID NO:27:

Cys Lys Gly Asp Xaa Pro Xaa
1               5

( 2 ) INFORMATION FOR SEQ ID NO:28:

( i ) SEQUENCE CHARACTERISTICS:
       ( A ) LENGTH: 7 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 5
       ( D ) OTHER INFORMATION: /note="This position is (2-Nal) or
             2-napthyl alanine."

( i x ) FEATURE:
       ( A ) NAME/KEY: Modified-site
       ( B ) LOCATION: 7
       ( D ) OTHER INFORMATION: /note="This position is C-NH2."

( x i ) SEQUENCE DESCRIPTION: SEQ ID NO:28:

Cys Lys Gly Asp Xaa Pro Xaa
1               5

( 2 ) INFORMATION FOR SEQ ID NO:29:

( i ) SEQUENCE CHARACTERISTICS:
       ( A ) LENGTH: 7 amino acids
       ( B ) TYPE: amino acid
       ( C ) STRANDEDNESS: single (D) TOPOLOGY: linear (ix) FEATURE:
    (A) NAME/KEY: Modified-site
    (B) LOCATION: 5
    (D) OTHER INFORMATION: /note="This position is (Cha) or cyclohexylanine."

(ix) FEATURE:
    (A) NAME/KEY: Modified-site
    (B) LOCATION: 7
    (D) OTHER INFORMATION: /note="This position is C-NH2."

(xi) SEQUENCE DESCRIPTION: SEQ ID NO:29:

```
Cys Lys Gly Asp Xaa Pro Xaa
1               5
```

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr or mercaptopropionyl."

(ix) FEATURE:
        (A) NAME/KEY: Modified-site
        (B) LOCATION: 7
        (D) OTHER INFORMATION: /note="This position is C-NH2."

(xi) SEQUENCE DESCRIPTION: SEQ ID NO:30:

```
Xaa Lys Gly Asp Trp Pro Xaa
1               5
```

(2) INFORMATION FOR SEQ ID NO:31:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr or mercaptopropionyl."

(ix) FEATURE:
        (A) NAME/KEY: Modified-site
        (B) LOCATION: 7
        (D) OTHER INFORMATION: /note="This position is C-NH2."

(xi) SEQUENCE DESCRIPTION: SEQ ID NO:31:

```
Xaa Lys Gly Asp Tyr Pro Xaa
1               5
```

(2) INFORMATION FOR SEQ ID NO:32:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1

(D) OTHER INFORMATION: /note="This position is Mpr or
mercaptopropionyl."

(ix) FEATURE:
    (A) NAME/KEY: Modified-site
    (B) LOCATION: 7
    (D) OTHER INFORMATION: /note="This position is C-NH2."

(xi) SEQUENCE DESCRIPTION: SEQ ID NO:32:

Xaa Lys Gly Asp Phe Pro Xaa
1                 5

(2) INFORMATION FOR SEQ ID NO:33:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Mpr or
        mercaptopropionyl."

(ix) FEATURE:
    (A) NAME/KEY: Modified-site
    (B) LOCATION: 7
    (D) OTHER INFORMATION: /note="This position is C-NH2."

(xi) SEQUENCE DESCRIPTION: SEQ ID NO:33:

Xaa Lys Gly Asp Leu Pro Xaa
1                 5

(2) INFORMATION FOR SEQ ID NO:34:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Mpr or
        mercaptopropionyl."

(ix) FEATURE:
    (A) NAME/KEY: Modified-site
    (B) LOCATION: 7
    (D) OTHER INFORMATION: /note="This position is C-NH2."

(xi) SEQUENCE DESCRIPTION: SEQ ID NO:34:

Xaa Lys Gly Asp Val Pro Xaa
1                 5

(2) INFORMATION FOR SEQ ID NO:35:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Mpr or
        mercaptopropionyl."

(ix) FEATURE:
    (A) NAME/KEY: Modified-site (B) LOCATION: 5
(D) OTHER INFORMATION: /note="This position is Tyr (OMe)."

(ix) FEATURE:
(A) NAME/KEY: Modified-site
(B) LOCATION: 7
(D) OTHER INFORMATION: /note="This position is C-NH2."

(xi) SEQUENCE DESCRIPTION: SEQ ID NO:35:

Xaa Lys Gly Asp Xaa Pro Xaa
1               5

(2) INFORMATION FOR SEQ ID NO:36:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 5
(D) OTHER INFORMATION: /note="This position is (2-Nal) or 2-napthyl alanine."

(ix) FEATURE:
(A) NAME/KEY: Modified-site
(B) LOCATION: 7
(D) OTHER INFORMATION: /note="This position is C-NH2."

(xi) SEQUENCE DESCRIPTION: SEQ ID NO:36:

Xaa Lys Gly Asp Xaa Pro Xaa
1               5

(2) INFORMATION FOR SEQ ID NO:37:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 5
(D) OTHER INFORMATION: /note="This position is (Cha) or cyclohexylanine."

(ix) FEATURE:
(A) NAME/KEY: Modified-site
(B) LOCATION: 7
(D) OTHER INFORMATION: /note="This position is C-NH2."

(xi) SEQUENCE DESCRIPTION: SEQ ID NO:37:

Xaa Lys Gly Asp Xaa Pro Xaa
1               5

(2) INFORMATION FOR SEQ ID NO:38:

(i) SEQUENCE CHARACTERISTICS:
(A) LENGTH: 6 amino acids (B) TYPE: amino acid
(C) STRANDEDNESS: single
(D) TOPOLOGY: cyclic (x i) SEQUENCE DESCRIPTION: SEQ ID NO:38:

Gly Lys Gly Asp Trp Pro
1               5

(2) INFORMATION FOR SEQ ID NO:39:

(i) SEQUENCE CHARACTERISTICS:
(A) LENGTH: 6 amino acids
(B) TYPE: amino acid
(C) STRANDEDNESS: single
(D) TOPOLOGY: cyclic (x i) SEQUENCE DESCRIPTION: SEQ ID NO:39:

Ala Lys Gly Asp Trp Pro
1               5

(2) INFORMATION FOR SEQ ID NO:40:

(i) SEQUENCE CHARACTERISTICS:
(A) LENGTH: 7 amino acids
(B) TYPE: amino acid
(C) STRANDEDNESS: single
(D) TOPOLOGY: cyclic (x i) SEQUENCE DESCRIPTION: SEQ ID NO:40:

Asp Ala Lys Gly Asp Trp Pro
1                   5

(2) INFORMATION FOR SEQ ID NO:41:

(i) SEQUENCE CHARACTERISTICS:
(A) LENGTH: 6 amino acids
(B) TYPE: amino acid
(C) STRANDEDNESS: single
(D) TOPOLOGY: cyclic (x i) SEQUENCE DESCRIPTION: SEQ ID NO:41:

Phe Lys Gly Asp Trp Pro
1               5

(2) INFORMATION FOR SEQ ID NO:42:

(i) SEQUENCE CHARACTERISTICS:
(A) LENGTH: 6 amino acids
(B) TYPE: amino acid
(C) STRANDEDNESS: single
(D) TOPOLOGY: cyclic (i x) FEATURE:
(A) NAME/KEY: Modified-site
(B) LOCATION: 1
(D) OTHER INFORMATION: /note="This position is beta-alanine."

(x i) SEQUENCE DESCRIPTION: SEQ ID NO:42:

Xaa Lys Gly Asp Trp Pro
1               5

(2) INFORMATION FOR SEQ ID NO:43:

(i) SEQUENCE CHARACTERISTICS:
(A) LENGTH: 6 amino acids
(B) TYPE: amino acid
(C) STRANDEDNESS: single
(D) TOPOLOGY: cyclic ( i x ) FEATURE:
        ( A ) NAME/KEY: Modified-site
        ( B ) LOCATION: 1
        ( D ) OTHER INFORMATION: /note="This position is gamma-Abu or gamma amino butyric acid."

( x i ) SEQUENCE DESCRIPTION: SEQ ID NO:43:

Xaa  Lys  Gly  Asp  Trp  Pro
1                           5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: cyclic ( x i ) SEQUENCE DESCRIPTION: SEQ ID NO:44:

Arg  Lys  Gly  Asp  Trp  Pro
1                           5

( 2 ) INFORMATION FOR SEQ ID NO:45:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 7
        ( D ) OTHER INFORMATION: /note="This position is C-NH2."

( x i ) SEQUENCE DESCRIPTION: SEQ ID NO:45:

Cys  Lys  Gly  Asp  Trp  Gly  Xaa
1                           5

( 2 ) INFORMATION FOR SEQ ID NO:46:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 7
        ( D ) OTHER INFORMATION: /note="This position is C-NH2."

( x i ) SEQUENCE DESCRIPTION: SEQ ID NO:46:

Cys  Lys  Ala  Asp  Trp  Pro  Xaa
1                           5

( 2 ) INFORMATION FOR SEQ ID NO:47:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 6
        ( D ) OTHER INFORMATION: /note="This position is (Sar) or sarcosine."

( i x ) FEATURE:
        ( A ) NAME/KEY: Modified-site (B) LOCATION: 7
(D) OTHER INFORMATION: /note="This position is C-NH2."

(xi) SEQUENCE DESCRIPTION: SEQ ID NO:47:

Cys Lys Gly Asp Trp Xaa Xaa
1               5

(2) INFORMATION FOR SEQ ID NO:48:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 7
(D) OTHER INFORMATION: /note="This position is C-NH2."

(xi) SEQUENCE DESCRIPTION: SEQ ID NO:48:

Cys Lys Gly Asp Ile Pro Xaa
1               5

(2) INFORMATION FOR SEQ ID NO:49:

(i) SEQUENCE CHARACTERISTICS:
(A) LENGTH: 6 amino acids
(B) TYPE: amino acid
(C) STRANDEDNESS: single
(D) TOPOLOGY: linear (ix) FEATURE:
(A) NAME/KEY: Modified-site
(B) LOCATION: 5
(D) OTHER INFORMATION: /note="This position is
(4-Cl-Phe)."

(ix) FEATURE:
(A) NAME/KEY: Modified-site
(B) LOCATION: 6
(D) OTHER INFORMATION: /note="This position is P-NH2."

(xi) SEQUENCE DESCRIPTION: SEQ ID NO:49:

Cys Lys Gly Asp Xaa Xaa
1               5

(2) INFORMATION FOR SEQ ID NO:50:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 3
(D) OTHER INFORMATION: /note="This position is (Sar) or
sarcosine."

(ix) FEATURE:
(A) NAME/KEY: Modified-site
(B) LOCATION: 7
(D) OTHER INFORMATION: /note="This position is C-NH2."

(xi) SEQUENCE DESCRIPTION: SEQ ID NO:50:

Cys Lys Xaa Asp Trp Pro Xaa
1               5

(2) INFORMATION FOR SEQ ID NO:51:

( i ) SEQUENCE CHARACTERISTICS:
- ( A ) LENGTH: 7 amino acids
- ( B ) TYPE: amino acid
- ( C ) STRANDEDNESS: single
- ( D ) TOPOLOGY: linear ( i x ) FEATURE:
- ( A ) NAME/KEY: Modified-site
- ( B ) LOCATION: 5
- ( D ) OTHER INFORMATION: /note="This position is (4-NO2-Phe)."

( i x ) FEATURE:
- ( A ) NAME/KEY: Modified-site
- ( B ) LOCATION: 7
- ( D ) OTHER INFORMATION: /note="This position is C-NH2."

( x i ) SEQUENCE DESCRIPTION: SEQ ID NO:51:

Cys Lys Gly Asp Xaa Pro Xaa
1               5

( 2 ) INFORMATION FOR SEQ ID NO:52:

( i ) SEQUENCE CHARACTERISTICS:
- ( A ) LENGTH: 7 amino acids
- ( B ) TYPE: amino acid
- ( C ) STRANDEDNESS: single
- ( D ) TOPOLOGY: linear ( i x ) FEATURE:
- ( A ) NAME/KEY: Modified-site
- ( B ) LOCATION: 1
- ( D ) OTHER INFORMATION: /note="This position is acetyl-cysteine."

( i x ) FEATURE:
- ( A ) NAME/KEY: Modified-site
- ( B ) LOCATION: 8
- ( D ) OTHER INFORMATION: /note="This position is C-NH2."

( x i ) SEQUENCE DESCRIPTION: SEQ ID NO:52:

Xaa Lys Gly Asp Trp Pro Xaa
1               5

( 2 ) INFORMATION FOR SEQ ID NO:53:

( i ) SEQUENCE CHARACTERISTICS:
- ( A ) LENGTH: 7 amino acids
- ( B ) TYPE: amino acid
- ( C ) STRANDEDNESS: single
- ( D ) TOPOLOGY: linear ( i x ) FEATURE:
- ( A ) NAME/KEY: Modified-site
- ( B ) LOCATION: 1
- ( D ) OTHER INFORMATION: /note="This position is Mpr or mercaptopropionyl."

( i x ) FEATURE:
- ( A ) NAME/KEY: Modified-site
- ( B ) LOCATION: 5
- ( D ) OTHER INFORMATION: /note="This position is Trp(Formyl)."

( i x ) FEATURE:
- ( A ) NAME/KEY: Modified-site
- ( B ) LOCATION: 7
- ( D ) OTHER INFORMATION: /note="This position is C-NH2."

( x i ) SEQUENCE DESCRIPTION: SEQ ID NO:53:

Xaa Lys Gly Asp Xaa Pro Xaa
1               5

( 2 ) INFORMATION FOR SEQ ID NO:54:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is mvl or mercaptovaleryl."

( i x ) FEATURE:
  ( A ) NAME/KEY: Modified-site
  ( B ) LOCATION: 7
  ( D ) OTHER INFORMATION: /note="This position is C-NH2."

( x i ) SEQUENCE DESCRIPTION: SEQ ID NO:54:

Xaa Lys Gly Asp Trp Pro Xaa
1                   5

( 2 ) INFORMATION FOR SEQ ID NO:55:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is Mpr or mercaptopropionyl."

( i x ) FEATURE:
  ( A ) NAME/KEY: Modified-site
  ( B ) LOCATION: 7
  ( D ) OTHER INFORMATION: /note="This position is Pen-NH2."

( x i ) SEQUENCE DESCRIPTION: SEQ ID NO:55:

Xaa Lys Gly Asp Trp Pro Xaa
1                   5

( 2 ) INFORMATION FOR SEQ ID NO:56:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note="This position is Mpr or mercaptopropionyl."

( i x ) FEATURE:
  ( A ) NAME/KEY: Modified-site
  ( B ) LOCATION: 7
  ( D ) OTHER INFORMATION: /note="This position is Pen+-NH2 or the D- isomer of Pen-NH2."

( x i ) SEQUENCE DESCRIPTION: SEQ ID NO:56:

Xaa Lys Gly Asp Trp Pro Xaa
1                   5

( 2 ) INFORMATION FOR SEQ ID NO:57:

( i ) SEQUENCE CHARACTERISTICS:
  ( A ) LENGTH: 7 amino acids
  ( B ) TYPE: amino acid (C) STRANDEDNESS: single
                (D) TOPOLOGY: linear (ix) FEATURE:
                (A) NAME/KEY: Modified-site
                (B) LOCATION: 1
                (D) OTHER INFORMATION: /note="This position is Mpr or
                    mercaptopropionyl."

(ix) FEATURE:
                (A) NAME/KEY: Modified-site
                (B) LOCATION: 4
                (D) OTHER INFORMATION: /note="This position is the D-isomer
                    of aspartic acid."

(ix) FEATURE:
                (A) NAME/KEY: Modified-site
                (B) LOCATION: 7
                (D) OTHER INFORMATION: /note="This position is Pen-NH2."

(xi) SEQUENCE DESCRIPTION: SEQ ID NO:57:

Xaa Lys Gly Xaa Trp Pro Xaa
 1               5

(2) INFORMATION FOR SEQ ID NO:58:

(i) SEQUENCE CHARACTERISTICS:
                (A) LENGTH: 7 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note="This position is Mpr or
                    mercaptopropionyl."

(ix) FEATURE:
                (A) NAME/KEY: Modified-site
                (B) LOCATION: 6
                (D) OTHER INFORMATION: /note="This position is (Thz) or
                    thiazolidine."

(ix) FEATURE:
                (A) NAME/KEY: Modified-site
                (B) LOCATION: 7
                (D) OTHER INFORMATION: /note="This position is C-NH2."

(xi) SEQUENCE DESCRIPTION: SEQ ID NO:58:

Xaa Lys Gly Asp Trp Xaa Xaa
 1               5

(2) INFORMATION FOR SEQ ID NO:59:

(i) SEQUENCE CHARACTERISTICS:
                (A) LENGTH: 7 amino acids
                (B) TYPE: amino acid
                (C) STRANDEDNESS: single
                (D) TOPOLOGY: linear (ix) FEATURE:
                (A) NAME/KEY: Modified-site
                (B) LOCATION: 1
                (D) OTHER INFORMATION: /note="This position is Mpr or
                    mercaptopropionyl."

(ix) FEATURE:
                (A) NAME/KEY: Modified-site
                (B) LOCATION: 5
                (D) OTHER INFORMATION: /note="This position is
                    Histidine (2,4-DNP)."

(ix) FEATURE:
                (A) NAME/KEY: Modified-site
                (B) LOCATION: 7

(D) OTHER INFORMATION: /note="This position is C-NH2."

(xi) SEQUENCE DESCRIPTION: SEQ ID NO:59:

Xaa Lys Gly Asp Xaa Pro Xaa
1               5

(2) INFORMATION FOR SEQ ID NO:60:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr or mercaptopropionyl."

(ix) FEATURE:
        (A) NAME/KEY: Modified-site
        (B) LOCATION: 5
        (D) OTHER INFORMATION: /note="This position is (2-Nal) or 2-naphthyl alanine."

(ix) FEATURE:
        (A) NAME/KEY: Modified-site
        (B) LOCATION: 7
        (D) OTHER INFORMATION: /note="This position is Pen-NH2."

(xi) SEQUENCE DESCRIPTION: SEQ ID NO:60:

Xaa Lys Gly Asp Xaa Pro Xaa
1               5

(2) INFORMATION FOR SEQ ID NO:61:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is mvl or mercaptovaleryl."

(ix) FEATURE:
        (A) NAME/KEY: Modified-site
        (B) LOCATION: 7
        (D) OTHER INFORMATION: /note="This position is Pen-NH2."

(xi) SEQUENCE DESCRIPTION: SEQ ID NO:61:

Xaa Lys Gly Asp Trp Pro Xaa
1               5

(2) INFORMATION FOR SEQ ID NO:62:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr or mercaptopropionyl."

(ix) FEATURE:
        (A) NAME/KEY: Modified-site (B) LOCATION: 6
(D) OTHER INFORMATION: /note="This position is (Pip) or pipecolic acid or 2-carboxypiperidine."

(ix) FEATURE:
(A) NAME/KEY: Modified-site
(B) LOCATION: 7
(D) OTHER INFORMATION: /note="This position is Pen-NH2."

(xi) SEQUENCE DESCRIPTION: SEQ ID NO:62:

Xaa Lys Gly Asp Trp Xaa Xaa
1               5

(2) INFORMATION FOR SEQ ID NO:63:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is (Har or homoarginine)."

(ix) FEATURE:
(A) NAME/KEY: Modified-site
(B) LOCATION: 7
(D) OTHER INFORMATION: /note="This position is C-NH2."

(xi) SEQUENCE DESCRIPTION: SEQ ID NO:63:

Xaa Xaa Gly Asp Trp Pro Xaa
1               5

(2) INFORMATION FOR SEQ ID NO:64:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 7
(D) OTHER INFORMATION: /note="This position is C+-NH2 or the D-isomer of cysteine-NH2."

(xi) SEQUENCE DESCRIPTION: SEQ ID NO:64:

Xaa Lys Gly Asp Trp Pro Xaa
1               5

(2) INFORMATION FOR SEQ ID NO:65:

(i) SEQUENCE CHARACTERISTICS:
(A) LENGTH: 7 amino acids
(B) TYPE: amino acid
(C) STRANDEDNESS: single
(D) TOPOLOGY: linear ( i x ) FEATURE:
  ( A ) NAME/KEY: Modified-site
  ( B ) LOCATION: 1
  ( D ) OTHER INFORMATION: /note="This position is Mpr or mercaptopropionyl."

( i x ) FEATURE:
  ( A ) NAME/KEY: Modified-site
  ( B ) LOCATION: 2
  ( D ) OTHER INFORMATION: /note="This position is K+ or D-isomer of lysine."

( i x ) FEATURE:
  ( A ) NAME/KEY: Modified-site
  ( B ) LOCATION: 7
  ( D ) OTHER INFORMATION: /note="This position is Pen-NH2."

( x i ) SEQUENCE DESCRIPTION: SEQ ID NO:65:

Xaa Xaa Gly Asp Trp Pro Xaa
1               5

( 2 ) INFORMATION FOR SEQ ID NO:66:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or mercaptopropionyl."

( i x ) FEATURE:
    ( A ) NAME/KEY: Modified-site
    ( B ) LOCATION: 2
    ( D ) OTHER INFORMATION: /note="This position is (Har or homoarginine)."

( i x ) FEATURE:
    ( A ) NAME/KEY: Modified-site
    ( B ) LOCATION: 7
    ( D ) OTHER INFORMATION: /note="This position is Pen-NH2."

( x i ) SEQUENCE DESCRIPTION: SEQ ID NO:66:

Xaa Xaa Gly Asp Trp Pro Xaa
1               5

( 2 ) INFORMATION FOR SEQ ID NO:67:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or mercaptopropionyl."

( i x ) FEATURE:
    ( A ) NAME/KEY: Modified-site
    ( B ) LOCATION: 2
    ( D ) OTHER INFORMATION: /note="This position is (Acetimidyl-Lys)."

( i x ) FEATURE:
    ( A ) NAME/KEY: Modified-site
    ( B ) LOCATION: 7
    ( D ) OTHER INFORMATION: /note="This position is C-NH2."

( x i ) SEQUENCE DESCRIPTION: SEQ ID NO:67:

Xaa Xaa Gly Asp Trp Pro Xaa
1               5

( 2 ) INFORMATION FOR SEQ ID NO:68:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or
         mercaptopropionyl."

( i x ) FEATURE:
    ( A ) NAME/KEY: Modified-site
    ( B ) LOCATION: 2
    ( D ) OTHER INFORMATION: /note="This position is
         (Acetimidyl-Lys)."

( i x ) FEATURE:
    ( A ) NAME/KEY: Modified-site
    ( B ) LOCATION: 7
    ( D ) OTHER INFORMATION: /note="This position is Pen-NH2."

( x i ) SEQUENCE DESCRIPTION: SEQ ID NO:68:

Xaa Xaa Gly Asp Trp Pro Xaa
1               5

( 2 ) INFORMATION FOR SEQ ID NO:69:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or
         mercaptopropionyl."

( i x ) FEATURE:
    ( A ) NAME/KEY: Modified-site
    ( B ) LOCATION: 2
    ( D ) OTHER INFORMATION: /note="This position is
         (NG,NG'-ethylene-Har) or NG,NG1-ethylene-homoarginine."

( i x ) FEATURE:
    ( A ) NAME/KEY: Modified-site
    ( B ) LOCATION: 7
    ( D ) OTHER INFORMATION: /note="This position is C-NH2."

( x i ) SEQUENCE DESCRIPTION: SEQ ID NO:69:

Xaa Xaa Gly Asp Trp Pro Xaa
1               5

( 2 ) INFORMATION FOR SEQ ID NO:70:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or
         mercaptopropionyl."

( i x ) FEATURE:
   ( A ) NAME/KEY: Modified-site
   ( B ) LOCATION: 2
   ( D ) OTHER INFORMATION: /note="This position is (NG,NG'-ethylene-Har) or NG,NG1-ethylene-homoarginine."

( i x ) FEATURE:
   ( A ) NAME/KEY: Modified-site
   ( B ) LOCATION: 7
   ( D ) OTHER INFORMATION: /note="This position is Pen-NH2."

( x i ) SEQUENCE DESCRIPTION: SEQ ID NO:70:

Xaa Xaa Gly Asp Trp Pro Xaa
1               5

( 2 ) INFORMATION FOR SEQ ID NO:71:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 1
      ( D ) OTHER INFORMATION: /note="This position is Mpr or mercaptopropionyl."

( i x ) FEATURE:
      ( A ) NAME/KEY: Modified-site
      ( B ) LOCATION: 2
      ( D ) OTHER INFORMATION: /note="This position is Har or homoarginine."

( i x ) FEATURE:
      ( A ) NAME/KEY: Modified-site
      ( B ) LOCATION: 3
      ( D ) OTHER INFORMATION: /note="This position is Sar or sarcosine."

( i x ) FEATURE:
      ( A ) NAME/KEY: Modified-site
      ( B ) LOCATION: 7
      ( D ) OTHER INFORMATION: /note="This position is C-NH2."

( x i ) SEQUENCE DESCRIPTION: SEQ ID NO:71:

Xaa Xaa Xaa Asp Trp Pro Xaa
1               5

( 2 ) INFORMATION FOR SEQ ID NO:72:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 1
      ( D ) OTHER INFORMATION: /note="This position is Mpr or mercaptopropionyl."

( i x ) FEATURE:
      ( A ) NAME/KEY: Modified-site
      ( B ) LOCATION: 2
      ( D ) OTHER INFORMATION: /note="This position is (Acetimidyl-Lys)."

( i x ) FEATURE:
      ( A ) NAME/KEY: Modified-site
      ( B ) LOCATION: 7
      ( D ) OTHER INFORMATION: /note="This position is Pen-NH2."

( x i ) SEQUENCE DESCRIPTION: SEQ ID NO:72:

Xaa Xaa Gly Asp Trp Pro Xaa
1                  5

( 2 ) INFORMATION FOR SEQ ID NO:73:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr or mercaptopropionyl."

( i x ) FEATURE:
        ( A ) NAME/KEY: Modified-site
        ( B ) LOCATION: 2
        ( D ) OTHER INFORMATION: /note="This position is (Phenylimidyl-Lys)."

( i x ) FEATURE:
        ( A ) NAME/KEY: Modified-site
        ( B ) LOCATION: 7
        ( D ) OTHER INFORMATION: /note="This position is C-NH2."

( x i ) SEQUENCE DESCRIPTION: SEQ ID NO:73:

Xaa Xaa Gly Asp Trp Pro Xaa
1                  5

( 2 ) INFORMATION FOR SEQ ID NO:74:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr or mercaptopropionyl."

( i x ) FEATURE:
        ( A ) NAME/KEY: Modified-site
        ( B ) LOCATION: 2
        ( D ) OTHER INFORMATION: /note="This position is Har or homoarginine."

( i x ) FEATURE:
        ( A ) NAME/KEY: Modified-site
        ( B ) LOCATION: 3
        ( D ) OTHER INFORMATION: /note="This position is Sar or sarcosine."

( i x ) FEATURE:
        ( A ) NAME/KEY: Modified-site
        ( B ) LOCATION: 7
        ( D ) OTHER INFORMATION: /note="This position is PenNH2."

( x i ) SEQUENCE DESCRIPTION: SEQ ID NO:74:

Xaa Xaa Xaa Asp Trp Pro Xaa
1                  5

( 2 ) INFORMATION FOR SEQ ID NO:75:

( i ) SEQUENCE CHARACTERISTICS:
        ( A ) LENGTH: 7 amino acids
        ( B ) TYPE: amino acid (C) STRANDEDNESS: single
          (D) TOPOLOGY: linear (ix) FEATURE:
          (A) NAME/KEY: Modified-site
          (B) LOCATION: 1
          (D) OTHER INFORMATION: /note="This position is Mpr or
                mercaptopropionyl."

(ix) FEATURE:
          (A) NAME/KEY: Modified-site
          (B) LOCATION: 2
          (D) OTHER INFORMATION: /note="This position is
          (Phenylimidyl-Lys)."

(ix) FEATURE:
          (A) NAME/KEY: Modified-site
          (B) LOCATION: 7
          (D) OTHER INFORMATION: /note="This position is PenNH2."

(xi) SEQUENCE DESCRIPTION: SEQ ID NO:75:

Xaa  Xaa  Gly  Asp  Trp  Pro  Xaa
    1                    5

(2) INFORMATION FOR SEQ ID NO:76:

(i) SEQUENCE CHARACTERISTICS:
          (A) LENGTH: 7 amino acids
          (B) TYPE: amino acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION: /note="This position is Mpr or
                mercaptopropionyl."

(ix) FEATURE:
          (A) NAME/KEY: Modified-site
          (B) LOCATION: 2
          (D) OTHER INFORMATION: /note="This position is Har or
                homoarginine."

(ix) FEATURE:
          (A) NAME/KEY: Modified-site
          (B) LOCATION: 6
          (D) OTHER INFORMATION: /note="This position is
                (3,4-dehydro-Pro)."

(ix) FEATURE:
          (A) NAME/KEY: Modified-site
          (B) LOCATION: 7
          (D) OTHER INFORMATION: /note="This position is C-NH2."

(xi) SEQUENCE DESCRIPTION: SEQ ID NO:76:

Xaa  Xaa  Gly  Asp  Trp  Xaa  Xaa
    1                    5

(2) INFORMATION FOR SEQ ID NO:77:

(i) SEQUENCE CHARACTERISTICS:
          (A) LENGTH: 5 amino acids
          (B) TYPE: amino acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION: /note="This position is Mpr or
                mercaptopropionyl."

(ix) FEATURE:
          (A) NAME/KEY: Modified-site
          (B) LOCATION: 2

( D ) OTHER INFORMATION: /note="This position is Har or
homoarginine."

( i x ) FEATURE:
( A ) NAME/KEY: Modified-site
( B ) LOCATION: 5
( D ) OTHER INFORMATION: /note="This position is Pen-NH2."

( x i ) SEQUENCE DESCRIPTION: SEQ ID NO:77:

Xaa Xaa Gly Asp Xaa
1                    5

( 2 ) INFORMATION FOR SEQ ID NO:78:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or
mercaptopropionyl."

( i x ) FEATURE:
( A ) NAME/KEY: Modified-site
( B ) LOCATION: 2
( D ) OTHER INFORMATION: /note="This position is
(Phenylimidyl-Lys)."

( i x ) FEATURE:
( A ) NAME/KEY: Modified-site
( B ) LOCATION: 5
( D ) OTHER INFORMATION: /note="This position is Pen-NH2."

( x i ) SEQUENCE DESCRIPTION: SEQ ID NO:78:

Xaa Xaa Gly Asp Xaa
1                    5

( 2 ) INFORMATION FOR SEQ ID NO:79:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or
mercaptopropionyl."

( i x ) FEATURE:
( A ) NAME/KEY: Modified-site
( B ) LOCATION: 3
( D ) OTHER INFORMATION: /note="This position is Har or
homoarginine."

( i x ) FEATURE:
( A ) NAME/KEY: Modified-site
( B ) LOCATION: 8
( D ) OTHER INFORMATION: /note="This position is C-NH2."

( x i ) SEQUENCE DESCRIPTION: SEQ ID NO:79:

Xaa Pro Xaa Gly Asp Trp Pro Xaa
1                    5

( 2 ) INFORMATION FOR SEQ ID NO:80:

( i ) SEQUENCE CHARACTERISTICS:
( A ) LENGTH: 8 amino acids ( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or mercaptopropionyl."

( i x ) FEATURE:
( A ) NAME/KEY: Modified-site
( B ) LOCATION: 3
( D ) OTHER INFORMATION: /note="This position is Har or homoarginine."

( i x ) FEATURE:
( A ) NAME/KEY: Modified-site
( B ) LOCATION: 8
( D ) OTHER INFORMATION: /note="This position is C-NH2."

( x i ) SEQUENCE DESCRIPTION: SEQ ID NO:80:

Xaa Gly Xaa Gly Asp Trp Pro Xaa
1               5

( 2 ) INFORMATION FOR SEQ ID NO:81:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or mercaptopropionyl."

( i x ) FEATURE:
( A ) NAME/KEY: Modified-site
( B ) LOCATION: 3
( D ) OTHER INFORMATION: /note="This position is Har or homoarginine."

( i x ) FEATURE:
( A ) NAME/KEY: Modified-site
( B ) LOCATION: 8
( D ) OTHER INFORMATION: /note="This position is C-NH2."

( x i ) SEQUENCE DESCRIPTION: SEQ ID NO:81:

Xaa Ala Xaa Gly Asp Trp Pro Xaa
1               5

( 2 ) INFORMATION FOR SEQ ID NO:82:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is Mpr or mercaptopropionyl."

( i x ) FEATURE:
( A ) NAME/KEY: Modified-site
( B ) LOCATION: 2
( D ) OTHER INFORMATION: /note="This position is Aib or alpha- aminoisobutyric acid."

( i x ) FEATURE:
( A ) NAME/KEY: Modified-site (B) LOCATION: 3
(D) OTHER INFORMATION: /note="This position is Har or homoarginine."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:82:

Xaa Xaa Xaa Gly Asp Trp Pro Xaa
1               5

(2) INFORMATION FOR SEQ ID NO:83:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is (N-Me-Arg)."

(ix) FEATURE:
(A) NAME/KEY: Modified-site
(B) LOCATION: 3
(D) OTHER INFORMATION: /note="This position is Har or homoarginine."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:83:

Xaa Xaa Xaa Gly Asp Trp Pro Xaa
1               5

(2) INFORMATION FOR SEQ ID NO:84:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is (N-Me-Ser)."

(ix) FEATURE:
(A) NAME/KEY: Modified-site
(B) LOCATION: 3
(D) OTHER INFORMATION: /note="This position is Har or homoarginine."

(ix) FEATURE:
(A) NAME/KEY: Modified-site (B) LOCATION: 8
(D) OTHER INFORMATION: /note="This position is C-NH2."

(xi) SEQUENCE DESCRIPTION: SEQ ID NO:84:

Xaa Xaa Xaa Gly Asp Trp Pro Xaa
1               5

(2) INFORMATION FOR SEQ ID NO:85:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is A+or the L- or D-isomer of alanine."

(ix) FEATURE:
(A) NAME/KEY: Modified-site
(B) LOCATION: 3
(D) OTHER INFORMATION: /note="This position is Har or homoarginine."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:85:

Xaa Xaa Xaa Gly Asp Trp Pro Xaa
1               5

(2) INFORMATION FOR SEQ ID NO:86:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is (beta-Ala)."

(ix) FEATURE:
(A) NAME/KEY: Modified-site
(B) LOCATION: 3
(D) OTHER INFORMATION: /note="This position is Har or homoarginine."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:86:

Xaa Xaa Xaa Gly Asp Trp Pro Xaa
1               5

(2) INFORMATION FOR SEQ ID NO:87:

(i) SEQUENCE CHARACTERISTICS:
      (A) LENGTH: 8 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 1
      (D) OTHER INFORMATION: /note="This position is Mpr or
         mercaptopropionyl."

(ix) FEATURE:
      (A) NAME/KEY: Modified-site
      (B) LOCATION: 2
      (D) OTHER INFORMATION: /note="This position is
         (N-Me-Leu)."

(ix) FEATURE:
      (A) NAME/KEY: Modified-site
      (B) LOCATION: 3
      (D) OTHER INFORMATION: /note="This position is Har or
         homoarginine."

(ix) FEATURE:
      (A) NAME/KEY: Modified-site
      (B) LOCATION: 8
      (D) OTHER INFORMATION: /note="This position is C-NH2."

(xi) SEQUENCE DESCRIPTION: SEQ ID NO:87:

Xaa Xaa Xaa Gly Asp Trp Pro Xaa
1               5

(2) INFORMATION FOR SEQ ID NO:88:

(i) SEQUENCE CHARACTERISTICS:
      (A) LENGTH: 8 amino acids
      (B) TYPE: amino acid
      (C) STRANDEDNESS: single
      (D) TOPOLOGY: linear (ix) FEATURE:
      (A) NAME/KEY: Modified-site
      (B) LOCATION: 1
      (D) OTHER INFORMATION: /note="This position is Mpr or
         mercaptopropionyl."

(ix) FEATURE:
      (A) NAME/KEY: Modified-site
      (B) LOCATION: 2
      (D) OTHER INFORMATION: /note="This position is
         (N-Me-Ala)."

(ix) FEATURE:
      (A) NAME/KEY: Modified-site
      (B) LOCATION: 3
      (D) OTHER INFORMATION: /note="This position is Har or
         homoarginine."

(ix) FEATURE:
      (A) NAME/KEY: Modified-site
      (B) LOCATION: 8
      (D) OTHER INFORMATION: /note="This position is C-NH2."

(xi) SEQUENCE DESCRIPTION: SEQ ID NO:88:

Xaa Xaa Xaa Gly Asp Trp Pro Xaa
1               5

(2) INFORMATION FOR SEQ ID NO:89:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i x ) FEATURE:
   ( A ) NAME/KEY: Modified-site
   ( B ) LOCATION: 1
   ( D ) OTHER INFORMATION: /note="This position is Mpr or mercaptopropionyl."

( i x ) FEATURE:
   ( A ) NAME/KEY: Modified-site
   ( B ) LOCATION: 2
   ( D ) OTHER INFORMATION: /note="This position is Sar."

( i x ) FEATURE:
   ( A ) NAME/KEY: Modified-site
   ( B ) LOCATION: 3
   ( D ) OTHER INFORMATION: /note="This position is Har or homoarginine."

( i x ) FEATURE:
   ( A ) NAME/KEY: Modified-site
   ( B ) LOCATION: 8
   ( D ) OTHER INFORMATION: /note="This position is C-NH2."

( x i ) SEQUENCE DESCRIPTION: SEQ ID NO:89:

Xaa Xaa Xaa Gly Asp Trp Pro Xaa
1               5

( 2 ) INFORMATION FOR SEQ ID NO:90:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i x ) FEATURE:
   ( A ) NAME/KEY: Modified-site
   ( B ) LOCATION: 1
   ( D ) OTHER INFORMATION: /note="This position is Mpr or mercaptopropionyl."

( i x ) FEATURE:
   ( A ) NAME/KEY: Modified-site
   ( B ) LOCATION: 3
   ( D ) OTHER INFORMATION: /note="This position is Har or homoarginine."

( i x ) FEATURE:
   ( A ) NAME/KEY: Modified-site
   ( B ) LOCATION: 8
   ( D ) OTHER INFORMATION: /note="This position is C-NH2."

( x i ) SEQUENCE DESCRIPTION: SEQ ID NO:90:

Xaa Val Xaa Gly Asp Trp Pro Xaa
1               5

( 2 ) INFORMATION FOR SEQ ID NO:91:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i x ) FEATURE:
   ( A ) NAME/KEY: Modified-site
   ( B ) LOCATION: 1
   ( D ) OTHER INFORMATION: /note="This position is Mpr or mercaptopropionyl."

( i x ) FEATURE:

(A) NAME/KEY: Modified-site
(B) LOCATION: 3
(D) OTHER INFORMATION: /note="This position is Har or homoarginine."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:91:

Xaa Ser Xaa Gly Asp Trp Pro Xaa
1               5

(2) INFORMATION FOR SEQ ID NO:92:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is Har or homoarginine."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:92:

Xaa Xaa Gly Asp Trp Pro Ala Xaa
1               5

(2) INFORMATION FOR SEQ ID NO:93:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 1
(D) OTHER INFORMATION: /note="This position is Mpr or mercaptopropionyl."

(ix) FEATURE:
(A) NAME/KEY: Modified-site
(B) LOCATION: 2
(D) OTHER INFORMATION: /note="This position is Har or homoarginine."

(ix) FEATURE:
(A) NAME/KEY: Modified-site
(B) LOCATION: 7
(D) OTHER INFORMATION: /note="This position is (N-Me-Ala)."

(ix) FEATURE:
(A) NAME/KEY: Modified-site
(B) LOCATION: 8
(D) OTHER INFORMATION: /note="This position is C-NH2."

(xi) SEQUENCE DESCRIPTION: SEQ ID NO:93:

```
Xaa Xaa Gly Asp Trp Pro Xaa Xaa
1               5
```

( 2 ) INFORMATION FOR SEQ ID NO:94:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr or mercaptopropionyl."

( i x ) FEATURE:
        ( A ) NAME/KEY: Modified-site
        ( B ) LOCATION: 2
        ( D ) OTHER INFORMATION: /note="This position is Har or homoarginine."

( i x ) FEATURE:
        ( A ) NAME/KEY: Modified-site
        ( B ) LOCATION: 8
        ( D ) OTHER INFORMATION: /note="This position is C-NH2."

( x i ) SEQUENCE DESCRIPTION: SEQ ID NO:94:

```
Xaa Xaa Gly Asp Trp Pro Gly Xaa
1               5
```

( 2 ) INFORMATION FOR SEQ ID NO:95:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr or mercaptopropionyl."

( i x ) FEATURE:
        ( A ) NAME/KEY: Modified-site
        ( B ) LOCATION: 2
        ( D ) OTHER INFORMATION: /note="This position is Har or homoarginine."

( i x ) FEATURE:
        ( A ) NAME/KEY: Modified-site
        ( B ) LOCATION: 7
        ( D ) OTHER INFORMATION: /note="This position is A+or the L- or D-isomer of alanine."

( i x ) FEATURE:
        ( A ) NAME/KEY: Modified-site
        ( B ) LOCATION: 8
        ( D ) OTHER INFORMATION: /note="This position is C-NH2."

( x i ) SEQUENCE DESCRIPTION: SEQ ID NO:95:

```
Xaa Xaa Gly Asp Trp Pro Xaa Xaa
1               5
```

( 2 ) INFORMATION FOR SEQ ID NO:96:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear (ix) FEATURE:
  (A) NAME/KEY: Modified-site
  (B) LOCATION: 1
  (D) OTHER INFORMATION: /note="This position is Mpr or mercaptopropionyl."

(ix) FEATURE:
  (A) NAME/KEY: Modified-site
  (B) LOCATION: 2
  (D) OTHER INFORMATION: /note="This position is Har or homoarginine."

(ix) FEATURE:
  (A) NAME/KEY: Modified-site
  (B) LOCATION: 8
  (D) OTHER INFORMATION: /note="This position is C-NH2."

(xi) SEQUENCE DESCRIPTION: SEQ ID NO:96:

Xaa Xaa Gly Asp Trp Pro Pro Xaa
1                   5

(2) INFORMATION FOR SEQ ID NO:97:

(i) SEQUENCE CHARACTERISTICS:
    (A) LENGTH: 8 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Mpr or mercaptopropionyl."

(ix) FEATURE:
    (A) NAME/KEY: Modified-site
    (B) LOCATION: 2
    (D) OTHER INFORMATION: /note="This position is Har or homoarginine."

(ix) FEATURE:
    (A) NAME/KEY: Modified-site
    (B) LOCATION: 7
    (D) OTHER INFORMATION: /note="This position is (Sar) or sarcosine."

(ix) FEATURE:
    (A) NAME/KEY: Modified-site
    (B) LOCATION: 8
    (D) OTHER INFORMATION: /note="This position is C-NH2."

(xi) SEQUENCE DESCRIPTION: SEQ ID NO:97:

Xaa Xaa Gly Asp Trp Pro Xaa Xaa
1                   5

(2) INFORMATION FOR SEQ ID NO:98:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Mpr or mercaptopropionyl."

(ix) FEATURE:
    (A) NAME/KEY: Modified-site
    (B) LOCATION: 2
    (D) OTHER INFORMATION: /note="This position is Har or homoarginine."

( i x ) FEATURE:
    ( A ) NAME/KEY: Modified-site
    ( B ) LOCATION: 7
    ( D ) OTHER INFORMATION: /note="This position is
    ( A i b )-NH2 or alpha- amino isobutyric acid-NH2."

( x i ) SEQUENCE DESCRIPTION: SEQ ID NO:98:

Xaa Xaa Gly Asp Trp Pro Xaa
1               5

( 2 ) INFORMATION FOR SEQ ID NO:99:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or
        mercaptopropionyl."

( i x ) FEATURE:
    ( A ) NAME/KEY: Modified-site
    ( B ) LOCATION: 3
    ( D ) OTHER INFORMATION: /note="This position is (Har or
        homoarginine)."

( i x ) FEATURE:
    ( A ) NAME/KEY: Modified-site
    ( B ) LOCATION: 8
    ( D ) OTHER INFORMATION: /note="This position is Pen-NH2."

( x i ) SEQUENCE DESCRIPTION: SEQ ID NO:99:

Xaa Ala Xaa Gly Asp Trp Pro Xaa
1               5

( 2 ) INFORMATION FOR SEQ ID NO:100:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or
        mercaptopropionyl."

( i x ) FEATURE:
    ( A ) NAME/KEY: Modified-site
    ( B ) LOCATION: 8
    ( D ) OTHER INFORMATION: /note="This position is Pen-NH2."

( x i ) SEQUENCE DESCRIPTION: SEQ ID NO:100:

Xaa Ala Lys Gly Asp Trp Pro Xaa
1               5

( 2 ) INFORMATION FOR SEQ ID NO:101:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or mercaptopropionyl."

( i x ) FEATURE:
  ( A ) NAME/KEY: Modified-site
  ( B ) LOCATION: 3
  ( D ) OTHER INFORMATION: /note="This position is (Har or
    homoarginine)."

( i x ) FEATURE:
  ( A ) NAME/KEY: Modified-site
  ( B ) LOCATION: 8
  ( D ) OTHER INFORMATION: /note="This position is Pen-NH2."

( x i ) SEQUENCE DESCRIPTION: SEQ ID NO:101:

Xaa Asp Xaa Gly Asp Trp Pro Xaa
1        5

( 2 ) INFORMATION FOR SEQ ID NO:102:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( x i ) SEQUENCE DESCRIPTION: SEQ ID NO:102:

Lys Gly Asp Trp
1

( 2 ) INFORMATION FOR SEQ ID NO:103:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( x i ) SEQUENCE DESCRIPTION: SEQ ID NO:103:

Arg Asp Gly Xaa
1

( 2 ) INFORMATION FOR SEQ ID NO:104:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 4
  ( D ) OTHER INFORMATION: /note="This position is W-NH2 or
    Trp-NH2."

( x i ) SEQUENCE DESCRIPTION: SEQ ID NO:104:

Arg Gly Asp Xaa
1

( 2 ) INFORMATION FOR SEQ ID NO:105:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: cyclic ( i x ) FEATURE:
  ( A ) NAME/KEY: Modified-site
  ( B ) LOCATION: 10
  ( D ) OTHER INFORMATION: /note="This position is A-NH2 or
    Ala-NH2."

( x i ) SEQUENCE DESCRIPTION: SEQ ID NO:105:

Gly Cys Gly Arg Gly Asp Trp Pro Cys Xaa
1               5                       10

( 2 ) INFORMATION FOR SEQ ID NO:106:

( i ) SEQUENCE CHARACTERISTICS:
          ( A ) LENGTH: 4 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 4
          ( D ) OTHER INFORMATION: /note="This position is W-NH2 or
                Trp-NH2."

( x i ) SEQUENCE DESCRIPTION: SEQ ID NO:106:

Lys Gly Asp Xaa
1

( 2 ) INFORMATION FOR SEQ ID NO:107:

( i ) SEQUENCE CHARACTERISTICS:
          ( A ) LENGTH: 10 amino acids
          ( B ) TYPE: amino acid
          ( C ) STRANDEDNESS: single
          ( D ) TOPOLOGY: cyclic ( i x ) FEATURE:
          ( A ) NAME/KEY: Modified-site
          ( B ) LOCATION: 10
          ( D ) OTHER INFORMATION: /note="This position is Ala-NH2."

( x i ) SEQUENCE DESCRIPTION: SEQ ID NO:107:

Gly Cys Gly Lys Gly Asp Trp Pro Cys Xaa
1               5                       10

( 2 ) INFORMATION FOR SEQ ID NO:108:

( i ) SEQUENCE CHARACTERISTICS:
          ( A ) LENGTH: 4 amino acids
          ( B ) TYPE: amino acid
          ( C ) STRANDEDNESS: single
          ( D ) TOPOLOGY: linear ( x i ) SEQUENCE DESCRIPTION: SEQ ID NO:108:

Arg Gly Asp Ser
1

( 2 ) INFORMATION FOR SEQ ID NO:109:

( i ) SEQUENCE CHARACTERISTICS:
          ( A ) LENGTH: 7 amino acids
          ( B ) TYPE: amino acid
          ( C ) STRANDEDNESS: single
          ( D ) TOPOLOGY: linear ( i x ) FEATURE:
          ( A ) NAME/KEY: Modified-site
          ( B ) LOCATION: 1
          ( D ) OTHER INFORMATION: /note="This position is Mpr or
                mercaptopropionyl."

( i x ) FEATURE:
          ( A ) NAME/KEY: Modified-site
          ( B ) LOCATION: 2
          ( D ) OTHER INFORMATION: /note="This position is (Har or
                homoarginine)."

( i x ) FEATURE:
          ( A ) NAME/KEY: Modified-site (B) LOCATION: 7
(D) OTHER INFORMATION: /note="This position is Pen-NH2."

(xi) SEQUENCE DESCRIPTION: SEQ ID NO:109:

Xaa Xaa Gly Asp Trp Pro Xaa
1               5

(2) INFORMATION FOR SEQ ID NO:110:

(i) SEQUENCE CHARACTERISTICS:
    (A) LENGTH: 9 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 9
    (D) OTHER INFORMATION: /note="This position is A-NH2 or Ala-NH2."

(xi) SEQUENCE DESCRIPTION: SEQ ID NO:110:

Gly Cys Gly Lys Gly Asp Trp Cys Xaa
1               5

(2) INFORMATION FOR SEQ ID NO:111:

(i) SEQUENCE CHARACTERISTICS:
    (A) LENGTH: 5 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Acetyl-Cys."

(ix) FEATURE:
    (A) NAME/KEY: Modified-site
    (B) LOCATION: 5
    (D) OTHER INFORMATION: /note="This position is C-NH2 or Cys-NH2."

(xi) SEQUENCE DESCRIPTION: SEQ ID NO:111:

Xaa Lys Gly Asp Xaa
1               5

(2) INFORMATION FOR SEQ ID NO:112:

(i) SEQUENCE CHARACTERISTICS:
    (A) LENGTH: 5 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is Acetyl-Cys."

(ix) FEATURE:
    (A) NAME/KEY: Modified-site
    (B) LOCATION: 5
    (D) OTHER INFORMATION: /note="This position is Pen-NH2."

(xi) SEQUENCE DESCRIPTION: SEQ ID NO:112:

Xaa Arg Gly Asp Xaa
1               5

(2) INFORMATION FOR SEQ ID NO:113:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 7
    ( D ) OTHER INFORMATION: /note="This position is C-NH2."

( x i ) SEQUENCE DESCRIPTION: SEQ ID NO:113:

Cys Lys Gly Glu Trp Pro Xaa
1               5

( 2 ) INFORMATION FOR SEQ ID NO:114:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 2
    ( D ) OTHER INFORMATION: /note="Xaa in position 2 is an Orn
        or ornithine."

( x i ) FEATURE:
    ( A ) NAME/KEY: Modified-site
    ( B ) LOCATION: 7
    ( C ) OTHER INFORMATION: /note="This position is C-NH2."

( x i ) SEQUENCE DESCRIPTION: SEQ ID NO:114:

Cys Xaa Gly Asp Trp Pro Xaa
1               5

( 2 ) INFORMATION FOR SEQ ID NO:115:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 3
    ( D ) OTHER INFORMATION: /note="This position is A+or the D-
        isomer of alanine."

( i x ) FEATURE:
    ( A ) NAME/KEY: Modified-site
    ( B ) LOCATION: 7
    ( D ) OTHER INFORMATION: /note="This position is C-NH2."

( x i ) SEQUENCE DESCRIPTION: SEQ ID NO:115:

Cys Lys Xaa Asp Trp Pro Xaa
1               5

( 2 ) INFORMATION FOR SEQ ID NO:116:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 2
    ( D ) OTHER INFORMATION: /note="This position is
        K(Formyl) or Lys (Formyl)."

( i x ) FEATURE:
        ( A ) NAME/KEY: Modified-site
        ( B ) LOCATION: 7
        ( D ) OTHER INFORMATION: /note="This position is C-NH2."

( x i ) SEQUENCE DESCRIPTION: SEQ ID NO:116:

Cys Xaa Gly Asp Trp Pro Xaa
1               5

( 2 ) INFORMATION FOR SEQ ID NO:117:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note="This position is (NMePhe)."

( i x ) FEATURE:
        ( A ) NAME/KEY: Modified-site
        ( B ) LOCATION: 7
        ( D ) OTHER INFORMATION: /note="This position is C-NH2."

( x i ) SEQUENCE DESCRIPTION: SEQ ID NO:117:

Cys Lys Gly Asp Xaa Pro Xaa
1               5

( 2 ) INFORMATION FOR SEQ ID NO:118:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 7
        ( D ) OTHER INFORMATION: /note="This position is C-NH2."

( x i ) SEQUENCE DESCRIPTION: SEQ ID NO:118:

Cys His Gly Asp Trp Pro Xaa
1               5

( 2 ) INFORMATION FOR SEQ ID NO:119:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="This position is Mpr or mercaptopropionyl."

( i x ) FEATURE:
        ( A ) NAME/KEY: Modified-site
        ( B ) LOCATION: 5
        ( D ) OTHER INFORMATION: /note="This position is W+or the D-isomer of Trp."

( i x ) FEATURE:
  ( A ) NAME/KEY: Modified-site
  ( B ) LOCATION: 7
  ( D ) OTHER INFORMATION: /note="This position is Pen-NH2."

( x i ) SEQUENCE DESCRIPTION: SEQ ID NO:119:

Xaa Lys Gly Asp Xaa Pro Xaa
1               5

( 2 ) INFORMATION FOR SEQ ID NO:120:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note="This position is Mpr or mercaptopropionyl."

( i x ) FEATURE:
    ( A ) NAME/KEY: Modified-site
    ( B ) LOCATION: 6
    ( D ) OTHER INFORMATION: /note="This position is P+ or the D-isomer of Proline."

( i x ) FEATURE:
    ( A ) NAME/KEY: Modified-site
    ( B ) LOCATION: 7
    ( D ) OTHER INFORMATION: /note="This position is Pen-NH2."

( x i ) SEQUENCE DESCRIPTION: SEQ ID NO:120:

Xaa Lys Gly Asp Trp Xaa Xaa
1               5